US009624188B2

(12) United States Patent
Balog et al.

(10) Patent No.: US 9,624,188 B2
(45) Date of Patent: Apr. 18, 2017

(54) IDO INHIBITORS

(71) Applicant: BRISTOL-MYERS SQUIBB COMPANY, Princeton, NJ (US)

(72) Inventors: James Aaron Balog, Lambertville, NJ (US); Audris Huang, New Hope, PA (US); Bin Chen, Lambertville, NJ (US); Libing Chen, Newtown, PA (US); Weifang Shan, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/775,976

(22) PCT Filed: Mar. 12, 2014

(86) PCT No.: PCT/US2014/023877
§ 371 (c)(1),
(2) Date: Sep. 14, 2015

(87) PCT Pub. No.: WO2014/150646
PCT Pub. Date: Sep. 25, 2014

(65) Prior Publication Data

US 2016/0060237 A1 Mar. 3, 2016

Related U.S. Application Data

(60) Provisional application No. 61/787,939, filed on Mar. 15, 2013.

(51) Int. Cl.

| | |
|---|---|
| ***C07D 305/06*** | (2006.01) |
| ***A61K 31/196*** | (2006.01) |
| ***C07C 275/42*** | (2006.01) |
| ***C07D 239/42*** | (2006.01) |
| ***C07D 241/42*** | (2006.01) |
| ***C07D 255/02*** | (2006.01) |
| ***A61K 31/337*** | (2006.01) |
| ***A61K 31/41*** | (2006.01) |
| ***A61K 31/42*** | (2006.01) |
| ***A61K 31/498*** | (2006.01) |
| ***A61K 31/505*** | (2006.01) |
| ***A61K 45/06*** | (2006.01) |
| ***C07D 261/14*** | (2006.01) |

(52) U.S. Cl.
CPC .......... *C07D 305/06* (2013.01); *A61K 31/196* (2013.01); *A61K 31/337* (2013.01); *A61K 31/41* (2013.01); *A61K 31/42* (2013.01); *A61K 31/498* (2013.01); *A61K 31/505* (2013.01); *A61K 45/06* (2013.01); *C07C 275/42* (2013.01); *C07D 239/42* (2013.01); *C07D 241/42* (2013.01); *C07D 255/02* (2013.01); *C07D 261/14* (2013.01); *C07C 2101/14* (2013.01)

(58) Field of Classification Search
CPC .. C07D 305/06; C07D 239/42; C07D 241/42; C07D 255/02; C07D 261/14; C07C 275/42; A61K 31/337; A61K 31/41; A61K 31/42; A61K 31/498; A61K 31/505; A61K 45/06
USPC ........................................................ 514/249
See application file for complete search history.

(56) References Cited

FOREIGN PATENT DOCUMENTS

| | | | |
|---|---|---|---|
| CN | 1354742 | A | 6/2002 |
| CN | 102083429 | A | 6/2011 |
| WO | WO02/46146 | A1 | 6/2002 |
| WO | WO2014/150677 | A1 | 9/2014 |

OTHER PUBLICATIONS

Rohrig et al Journal of Medicinal Chemistry, 2015, 58, 9421-9437.*

* cited by examiner

*Primary Examiner* — Yevegeny Valenrod
(74) *Attorney, Agent, or Firm* — Serena Farquharson-Torres; Maureen S. Gibbons

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention. Formula (I).

(I)

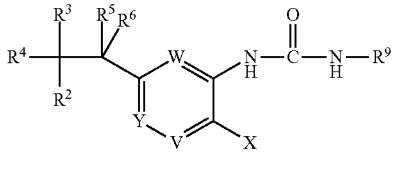

11 Claims, No Drawings

IDO INHIBITORS

CROSS-REFERENCE TO RELATED APPLICATIONS

This application claims the benefit of U.S. Provisional Application No. 61/787,939, filed Mar. 15, 2013, the disclosure of which is incorporated herein by reference in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. Indoleamine-2,3-dioxygenase is a heme-containing intracellular enzyme that catalyzes the first and rate-determining step in the degradation of the essential amino acid L-tryptophan to N-formyl-kynurenine. N-formyl-kynurenine is then metabolized by multiple steps to eventually produce nicotinamide adenine dinucleotide (NAD+). Tryptophan catabolites produced from N-formyl-kynurenine, such as kynurenine, are known to be preferentially cytotoxic to T-cells. Thus an overexpression of IDO can lead to increased tolerance in the tumor microenvironment. IDO overexpression has been shown to be an independent prognostic factor for decreased survival in patients with melanoma, pancreatic, colorectal and endometrial cancers among others. Moreover, IDO has been found to be implicated in neurologic and psychiatric disorders including mood disorders as well as other chronic diseases characterized by IDO activation and tryptophan depletion, such as viral infections, for example AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting production of IDO would be a most welcomed addition to the physician's armamentarium.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO inhibition, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides compounds of Formula (I)

(I)

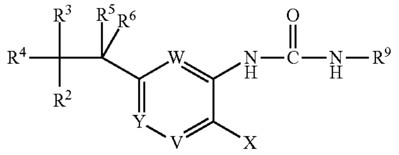

wherein

X is

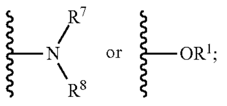

W is N or $CR^{10}$;

Y is N or $CR^{11}$;

V is N or $CR^{12}$;

$R^1$ is optionally substituted aryl-$C_1$-$C_{10}$-alkyl, or optionally substituted aryl;

$R^2$ is —$CO_2H$, optionally substituted heterocyclyl, optionally substituted —$CONHSO_2R^{14}$, optionally substituted —$CONHCOR^{13}$, optionally substituted —$SO_2NHCOR^{13}$ or optionally substituted —$NHSO_2R^{14}$;

$R^{13}$ is optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^{14}$ is $CF_3$ or optionally substituted $C_1$-$C_{10}$ alkyl;

$R^3$ is H, halo, CN, optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^4$ is H or optionally substituted $C_1$-$C_{10}$ alkyl;

$R^5$ and $R^6$ are independently H, optionally substituted $C_1$-$C_{10}$ alkyl or OH, or $R^5$ and $R^6$ are taken together with the carbon to which they are attached to form

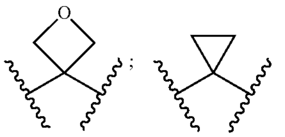 [SMILES: *C1(*)COC1 ; *C1(*)CC1]

$R^7$ and $R^8$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, or optionally substituted $C_3$-$C_8$ cycloalkyl;

$R^9$ is optionally substituted aryl, optionally substituted $C_1$-$C_{10}$ alkylaryl, optionally substituted $C_1$-$C_{10}$ alkoxyaryl, optionally substituted heteroaryl, optionally substituted $C_1$-$C_{10}$-alkyl heteroaryl, optionally substituted aryl-$C_1$-$C_{10}$-alkylaryl, optionally substituted aryloxyaryl, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, or optionally substituted $C_4$-$C_8$ cycloalkenyl;

$R^{10}$, $R^{11}$ and $R^{12}$ are H;

and/or a stereoisomer, a tautomer or a pharmaceutically acceptable salt thereof.

In a second aspect, the invention provides a compound of Formula (I) or (II) within the scope of the first aspect (II)

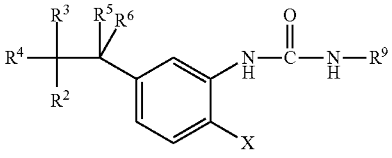

wherein

X is

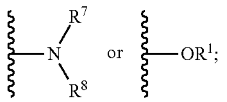

$R^1$ is optionally substituted aryl-$C_1$-$C_{10}$-alkyl, or optionally substituted aryl;

$R^2$ is —$CO_2H$, optionally substituted heterocyclyl, optionally substituted —$CONHSO_2R^{14}$, optionally substituted —$CONHCOR^{13}$, optionally substituted —$SO_2NHCOR^{13}$ or optionally substituted —$NHSO_2R^{14}$;

$R^{13}$ is optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^{14}$ is $CF_3$ or optionally substituted $C_1$-$C_{10}$ alkyl;

$R^3$ is H, halo, CN, optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^4$ is H or optionally substituted $C_1$-$C_{10}$ alkyl;

$R^5$ and $R^6$ are independently H, optionally substituted $C_1$-$C_{10}$ alkyl or OH, or $R^5$ and $R^6$ are taken together with the carbon to which they are attached to form

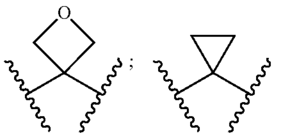 [SMILES: *C1(*)COC1 ; *C1(*)CC1]

$R^7$ and $R^8$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, or optionally substituted $C_3$-$C_8$ cycloalkyl;

$R^9$ is optionally substituted aryl, optionally substituted $C_1$-$C_{10}$ alkylaryl, optionally substituted $C_1$-$C_{10}$ alkoxyaryl, optionally substituted heteroaryl, optionally substituted $C_1$-$C_{10}$-alkyl heteroaryl, optionally substituted aryl-$C_1$-$C_{10}$-alkylaryl, optionally substituted aryloxyaryl, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, or optionally substituted $C_4$-$C_8$ cycloalkenyl;

$R^{10}$, $R^{11}$ and $R^{12}$ are H;

and/or a stereoisomer, a tautomer or a pharmaceutically acceptable salt thereof.

In a third aspect, the invention provides a compound of Formula (I) or (II) within the scope of the first and second aspects wherein X is $NR^7R^8$ and/or a stereoisomer, a tautomer or a pharmaceutically acceptable salt thereof.

In a fourth aspect, the invention provides a compound of Formula (I) or (II) within the scope of the first and second aspects wherein X is $OR^1$ and/or a stereoisomer, a tautomer or a pharmaceutically acceptable salt thereof.

In a fifth aspect, the invention provides a compound of Formula (I) or (II) within the scope of the first, second and third aspects wherein X is $NR^7R^8$;

$R^2$ is $CO_2H$ or

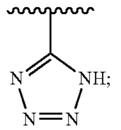

$R^3$ is H or $C_1$-$C_6$ alkyl;

$R^4$ is H or $C_1$-$C_6$ alkyl;

$R^5$ and $R^6$ are independently H, $C_1$-$C_6$ alkyl, $CF_3$ or OH, or $R^5$ and $R^6$ are taken together with the carbon to which they are attached to form

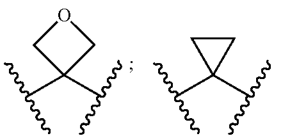 [SMILES: *C1(*)COC1 ; *C1(*)CC1]

$R^7$ and $R^8$ are independently selected from $C_1$-$C_6$ alkyl, $C_1$-$C_6$-alkoxy-$C_1$-$C_{10}$ alkyl, $C_1$-$C_6$ alkoxy, or optionally substituted aryl-$C_1$-$C_6$-alkyl;

$R^9$ is aryl, $C_1$-$C_6$ alkylaryl, $C_1$-$C_6$ alkoxyaryl, or optionally substituted heteroaryl;

and/or a stereoisomer, a tautomer or a pharmaceutically acceptable salt thereof.

In a sixth aspect, the invention provides a compound of Formula (I) or (II) within the scope of one or more previous aspects wherein $R^2$ is $CO_2H$ or

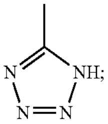

$R^3$ is H or $CH_3$;

$R^4$ is H or $CH_3$;

$R^5$ and $R^6$ are independently selected from

H, $CH_3$, $CF_3$, or

OH, or $R^5$ and $R^6$ are taken together with the carbon to which they are attached to form

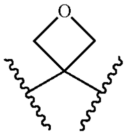 ; 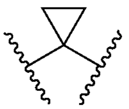

$R^7$ and $R^8$ are independently selected from

H,

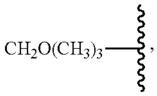, 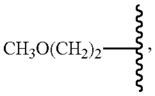, 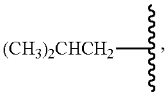, or 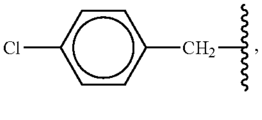, $R^9$ is

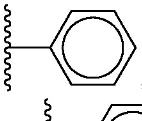, 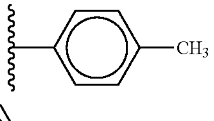, 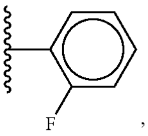, 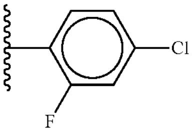, 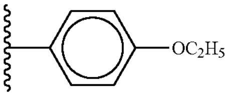, 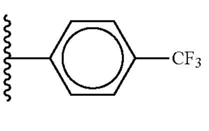, 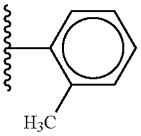, -continued

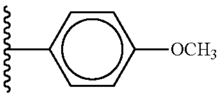, 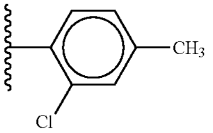, 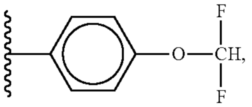 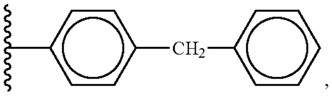, 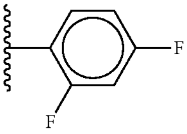, 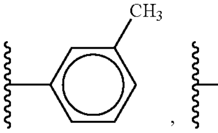, 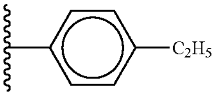, 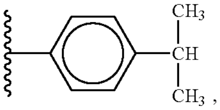, 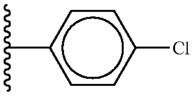, 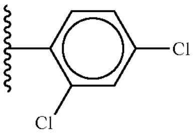, 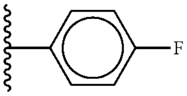, 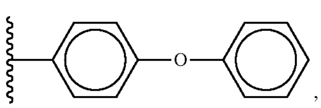, 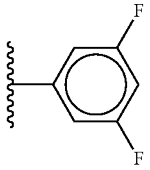, 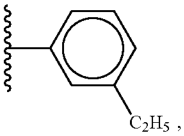, 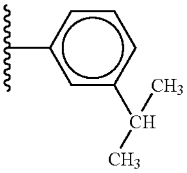, 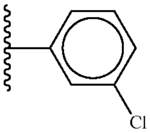, 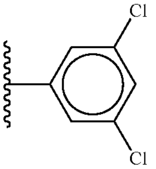, or 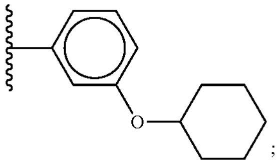;

$R^{10}$ is H;

$R^{11}$ is H; and $R^{12}$ is H;

and/or a pharmaceutically acceptable salt thereof, a stereoisomer thereof or a tautomer thereof.

In another aspect, the invention provides a compound of Formula (I) or (II) within the scope of one or more previous aspects wherein X is $OR^1$;

$R^1$ is aryl-$C_1$-$C_6$-alkyl or aryl($C_3$-$C_8$ cycloalkyl)$C_1$-$C_6$ alkyl;

$R^2$ is $CO_2H$;

$R^3$ is H;

$R^4$ is H;

$R^5$ and $R^6$ are independently selected from H or $C_1$-$C_6$ alkyl;

$R^9$ is $C_1$-$C_6$ alkylaryl or haloaryl;

and/or a stereoisomer, a tautomer or a pharmaceutically acceptable salt thereof.

In another aspect, the invention provides a compound of Formula (I) or (II) within the scope of one or more previous aspects wherein $R^2$ is $CO_2H$;

$R^3$ is H;

$R^4$ is H;

$R^5$ and $R^6$ are independently selected from H or $CH_3$;

$R^4$ is

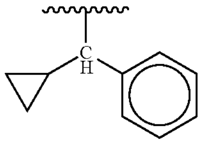,
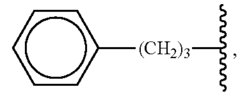, or
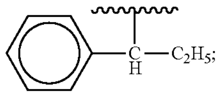;

$R^9$ is

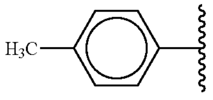 or
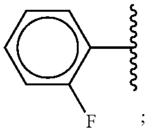;

$R^{10}$ is H;

$R^{11}$ is H; and $R^{12}$ is H;

and/or a pharmaceutically acceptable salt thereof, a stereoisomer thereof or a tautomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO $IC_{50}$ values≤250 nM.

In another embodiment, the compounds of the invention have human IDO $IC_{50}$ values≤50 nM.

In another embodiment, the compounds of the invention have human IDO $IC_{50}$ values≤20 nM.

In another embodiment, the compounds of the invention have human IDO $IC_{50}$ values≤10 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, anti-metabolites (including, without limitation, folic acid antagonists, pyrimidine analogs, purine analogs and adenosine de-aminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to co-stimulatory molecules such as CTLA-4, 4-1BB and PD-1, or antibodies to cytokines (IL-10 or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.,* 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.,* 1(8):792-797 (1995)); (iv) inhibitors of Akt family kinases or the Akt pathway, such as, for example, rapamycin (see, for example, Sekulic et al., *Cancer Res.,* 60:3504-3513 (2000)); (v) cell cycle kinase inhibitors such as, for example, flavopiridol and UCN-O1 (see, for example, Sausville, *Curr. Med. Chem. Anti-Canc. Agents,* 3:47-56 (2003)); and (vi) phosphatidyl inositol kinase inhibitors such as, for example, LY294002

(see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddl); zalcitabine (ddC); stavudine (d4T); lamivudine (3TC); abacavir (1592U89); adefovir dipivoxil [bis (POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

DEFINITIONS

Unless specifically stated otherwise herein, references made in the singular may also include the plural. For example, “a” and “an” may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as “optionally substituted”, the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —$SO_2NH_2$, substituted sulfonamido, nitro, cyano, carboxy, carbamyl, e.g. —$CONH_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —$CONH_2$ is attached through the carbon atom.

Additionally, for purposes of clarity, when there is no substituent shown at the end of a solid line, this indicates that there is a methyl ($CH_3$) group connected to the bond.

As used herein, the term “alkyl” or “alkylene” is intended to include both branched and straight-chain saturated aliphatic hydrocarbon groups having the specified number of carbon atoms. For example, “$C_1$-$C_6$ alkyl” denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "$C_2$-$C_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

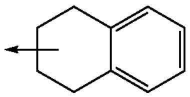
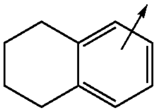
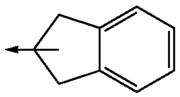
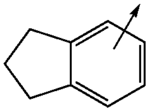

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), CONH($C_{1-4}$ alkyl), CON($C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C═C, C═N, or N═N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). Prodrugs and Targeted Delivery (Methods and Principles in Medicinal Chemistry), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or non-stoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Hex | hexanes |
| MeOH | methanol |
| EtOH | ethanol |
| i-PrOH or IPA | isopropanol |
| AcOH or HOAc | acetic acid |
| $CDCl_3$ | deutero-chloroform |
| $CHCl_3$ | chloroform |
| cDNA | complimentary DNA |
| DMF | dimethyl formamide |
| DMSO | dimethyl sulfoxide |
| DIAD | Diisopropyl azodicarboxylate |

-continued

| | |
|---|---|
| EDTA | ethylenediaminetetraacetic acid |
| EtOAc | ethyl acetate |
| $Et_2O$ | diethyl ether |
| $AlCl_3$ | aluminum chloride |
| Boc | tert-butyloxycarbonyl |
| $CH_2Cl_2$ | dichloromethane |
| $CH_3CN$ or ACN | acetonitrile |
| $Cs_2CO_3$ | cesium carbonate |
| HCl | hydrochloric acid |
| $H_2SO_4$ | sulfuric acid |
| $K_2CO_3$ | potassium carbonate |
| mCPBA or m-CPBA | meta-chloroperbenzoic acid |
| Pd/C | palladium on carbon |
| Hunig's base | diisopropylethylamine |
| PS | polystyrene |
| $SiO_2$ | silica oxide |
| $SnCl_2$ | tin(II) chloride |
| TEA | triethylamine |
| TFA | trifluoroacetic acid |
| TFAA | trifluoroacetic anhydride |
| THF | tetrahydrofuran |
| $TMSCHN_2$ | trimethylsilyldiazomethane |
| KOAc | potassium acetate |
| $MgSO_4$ | magnesium sulfate |
| NMP | N-Methylpyrrolidone |
| MsOH or MSA | methylsulfonic acid |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |
| $NH_3$ | ammonia |
| $NH_4Cl$ | ammonium chloride |
| $NH_4OH$ | ammonium hydroxide |
| LG | leaving group |
| RT | room temperature |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The Compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Greene, T. W. et al., *Protecting Groups in Organic Synthesis,* 3rd Edition, Wiley (1999)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure.* 4th Edition, Wiley & Sons, New York, N.Y. (1992); Katritzky, A. R. et al., eds., *Comprehensive Organic Functional Groups Transformations,* 1st Edition, Elsevier Science Inc., Tarrytown, N.Y. (1995); Larock, R. C., *Comprehensive Organic Transformations*, VCH Publishers, Inc., New York, N.Y. (1989), and references therein.

Compounds (i), where X═F and Z can be Br, Cl and I are commercially available or can be prepared utilizing standard transformations known to those of ordinary proficiency in the art of organic/medicinal chemistry. Treatment of compounds (i), with amines $HNR^7R^8$ (Scheme 1) and a suitable base in a solvent such as THF, DMF, NMP, or the like affords intermediates (ii). Generally heating is required. Suitable bases include, but are not limited to aliphatic tertiary amines or an excess of the reacting primary or secondary amine $HNR^7R^8$. Treatment of compounds (ii) under standard Heck palladium coupling conditions such as a $Pd^{II}$ catalyst $Pd(OAc)_2$ and olefin containing compounds (iii) in a solvent such as THF, yields compounds (iv). Reduction of the olefin and the nitroaromatic found in compounds (iv) can be reduced under reductive conditions such as but not limited to Pd/C under an atmosphere of $H_2$ and in a solvent such as ethyl acetate or methanol to afford saturated aniline compounds (v). Treatment of anilines (v) with an isocyanate $R^9N═C═O$, affords urea compounds (vi). Typically, this reaction is performed in a solvent such as THF at a temperature between ambient and the boiling point of the solvent. Esters (vi) may be converted to the corresponding carboxylic acids of the invention I under various conditions familiar to those of ordinary skill in the art. Generally this is effected using an alkali metal hydroxide (MOH) in aqueous solution, preferably with an organic co-solvent such as methanol or THF.

Scheme 1

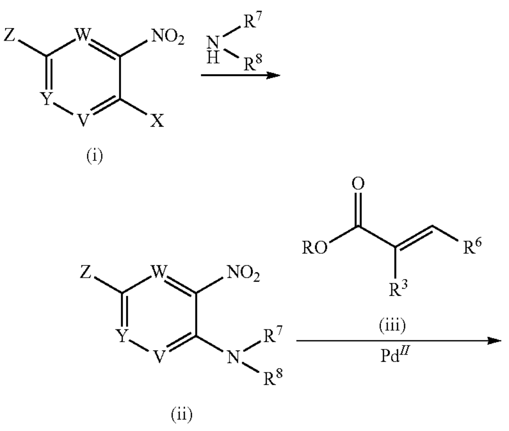

(i)

(ii)

-continued

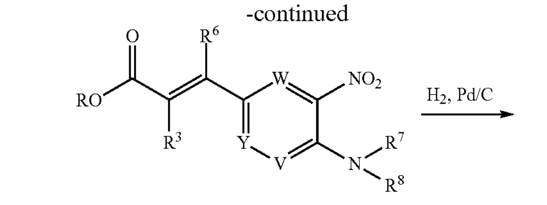

(iv)

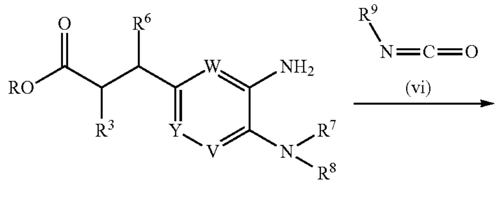

(v)

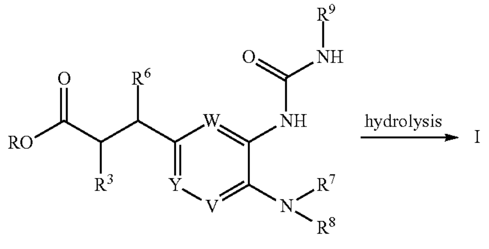

(vii)

Treatment of compounds carbonyl containing compounds (vii), where X═F and Z can be Br, Cl and I, with amines $HNR^7R^8$ (Scheme 1) and a suitable base in a solvent such as THF, DMF, NMP, or the like affords intermediates (ii). Generally heating is required. Suitable bases include, but are not limited to aliphatic tertiary amines or an excess of the reacting primary or secondary amine $HNR^7R^8$. Olefination of the carbonyl aldehyde or ketone can be accomplished by many methods that are well-known to those skilled in the art, such as Horner-Wadsworth-Emmons conditions as shown in Scheme 2. In practice the carbonyl compounds (ix) can be treated with a phosphonic ester (x) in the presence of a base such as sodium hexamethyldisilazane (NaHMDS) to afford olefins (iv). Olefins (iv) can be converted to compounds of the invention I by methods described in Scheme 1.

Scheme 2

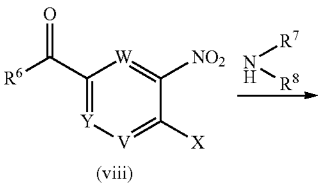

(viii)

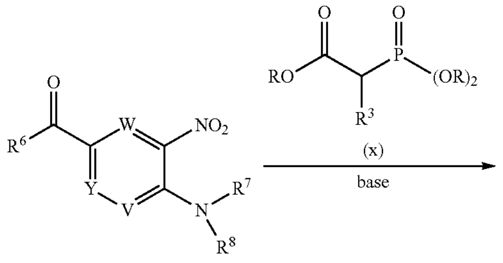

(ix)

-continued

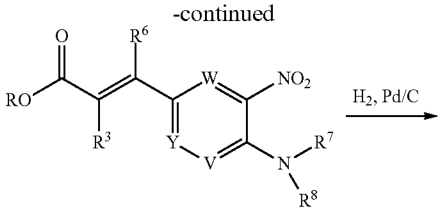

(iv)

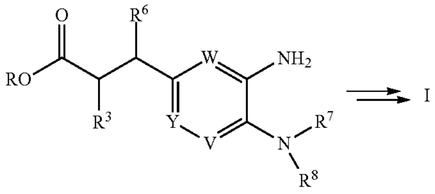

(v)

In Scheme 3 reduction of the nitro group in compounds (ii) to afford anilines (xi) can be effected by various means including catalytic hydrogenation and dissolving metal reductions both in their various forms. See: Modern Synthetic Reactions, Second Edition by Herbert O. House, Benjamin Cummings, Menlo Park, Calif., 1972. A preferred method for effecting this reduction without removal of the halogen substituent Z involves stirring a solution of (ii) in a wet alcoholic solvent with an acid such as ammonium chloride and finely divided zinc. The anilines (xi) can be couple to the olefins (xii) under standard Heck coupling conditions with a $Pd^{II}$ catalyst such as $Pd(OAc)_2$ to afford the olefins (xiii). The aniline compounds (xiii) can then be converted to compounds of the invention I by treatment with an isocyanate as previously described.

Scheme 3

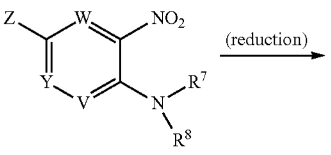

(ii)

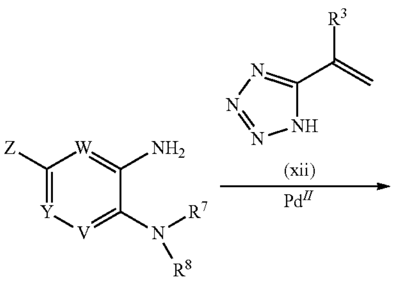

(xi)

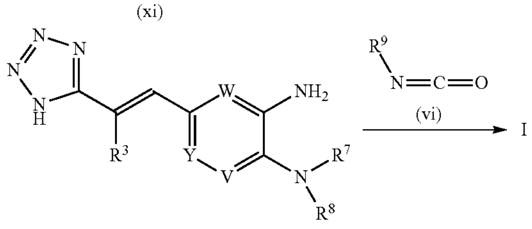

(xiii)

As shown in Scheme 4, compounds (v) (prepared by the methods described above) may be coupled with carboxylic acids using peptide coupling reagents such as Bop, Pybop, HATU or a similar reagent and a suitable base in a solvent such as THF, DMF, NMP, or the like to afford intermediates (xv). The use of such peptide coupling reagents has been reviewed by Han, S-Y et al., *Tetrahedron,* 60:2447-2467 (2004). Suitable bases include, but are not limited to aliphatic tertiary amines. Alternatively, amines (v) could react with acid chlorides of the formula $R^9CH_2COCl$ to give amides (xv), again in a solvent in the presence of a base. Conversion of (xv) to compounds of the invention I is accomplished by hydrolysis of the ester by methods described previously to afford a compound of the invention I.

Scheme 4

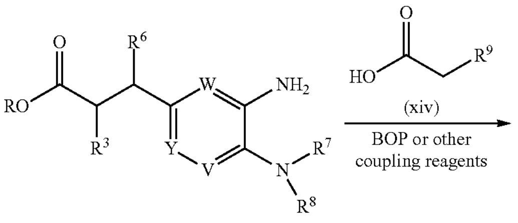

(v)

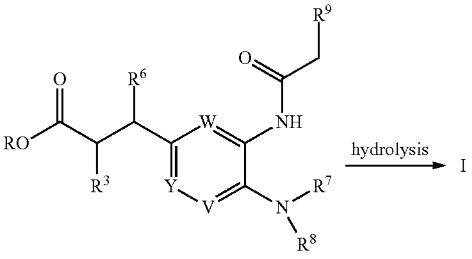

(xv)

In Scheme 5, compounds (iv) may be treated with an appropriate organometallic, such as a cuprate, to afford compounds (xvi) where R5 has been installed beta to the ester carbonyl. These reactions are well known to those skilled in the art and comprise an alkyl or aryl Grignard reagent such as $^5R$—MgBr and a $Cu^I$ reagent such as Copper(I)iodide. The cuprate that is so-formed can then add in a 1,4 sense to the unsaturated ester (iv) to give the compounds (xvi) which can be converted to compounds of the Invention I by methods described previously.

Scheme 5

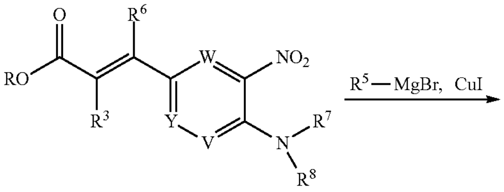

(iv)

-continued

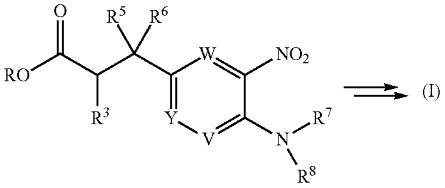

(xvi)

Scheme 6 below demonstrates the preparation of compounds of the invention I where $R^5$ and $R^6$ have been joined to form a cyclpropane. The benzyl bromide xvii can be purchased or synthesized by one of ordinary skills in the art. Treatment of (xvii) with a cyanide anion source, such as potassium cyanide, in the presence of a base, such as potassium carbonate will afford the nitrile compounds xviii. Treatment of xviii with $HNR^7R^8$, as described previously will afford the amine compounds (xix). Cyclpropane formation can be accomplished by several methods known to one skilled in the art. One method uses 1-bromo-2-chloroethane in the presence of a strong base such as sodium hydride to afford the cyclopropane (xx). Hydrolysis of the nitrile xx can be accomplished by first treating with a strong base, such as potassium hyroxide, at elevated temperatures to afford the corresponding carboxylic acids (xxi). A one carbon homologation of the acids (xxi) can be accomplished by several methods known to one skilled in the art. Scheme 6 depicts a three step process from xxi to produce the homologated analogs (xxii) (Qiao, J. et al PCT Int Appl, 2003099276. The acids xxii can then be converted to compounds of the invention I by methods discussed previously.

Scheme 6

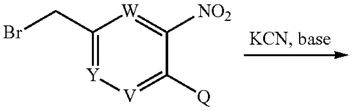

(xvii)

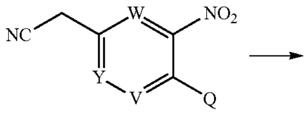

(xviii)

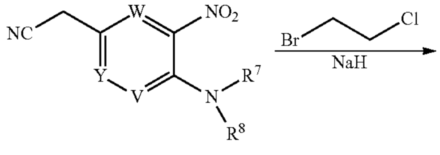

(xix)

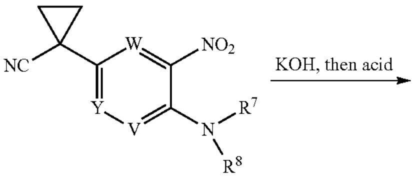

(xx)

-continued

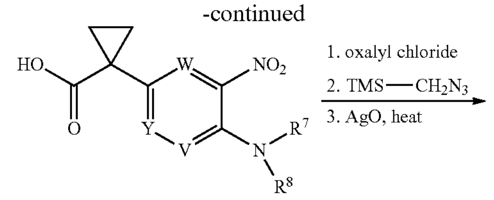

(xxi)

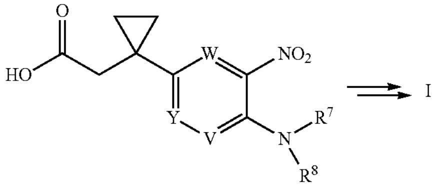

(xxii)

Scheme 7 below shows the preparation of oxetane compounds of the invention I. 2-oxetanone is commercially available and can be treated under standard Horner-Wadsworth Emmons olefination conditions using a phosphonate (x) in the presence of a base such as lithium hexamethyldisilazane (LiHMDS) to afford the unsaturated ester (xxxiv). Rhodium catalyzed 1,4-conjugate addition of a boronic acid (xxv) and an unsaturated ester (xxiv) are well known (Zou, G. et al Dalton Trans. (28), 3055, 2007) and can be accomplished using a rhodium$^{II}$ catalyst, for example, $Rh(COD)_2Cl]_2$ in the presence of a strong base such as KOH to afford the oxetanes (xxvi) with an exocyclic olefin. The oxetanes (xxvi) can be converted to compounds of the invention I by methods previously described.

Scheme 7.

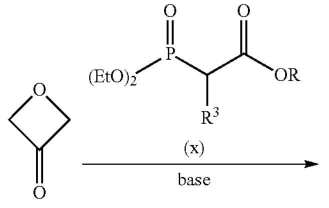

(xiii)

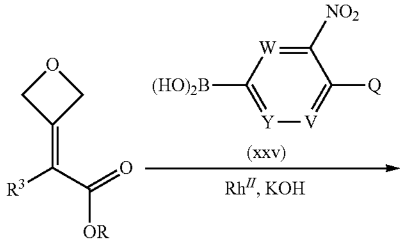

(xxiv)

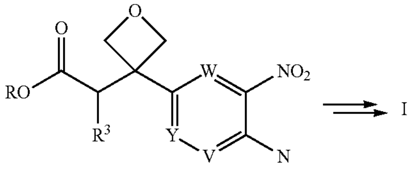

(xxvi)

Scheme 8 depicts the preparation of compounds of the invention I where X═OR$^1$. Compounds (xxvii), which can be purchased, can be treated with an allyl halide (xxviii) such as allyl iodide and a base, such as potassium carbonate, in solvent such as DMF to afford the alkyl ether (xxix). Heating may be required for ether formation. The allyl ether xxix can be encouraged to undergo a [3,3]-sigmatropic rearrangement by heating to high temperatures, for example 155° C. in a solvent such as diglyme to afford the phenolic compounds (xxx) with the allyl group transferred to the adjacent ortho position of the aryl ring. The phenol (xxx) can be treated with a base and an alkyl halide $R^1$—Z in a solvent such as THF at room temperature or elevated temperatures to afford the aryl ethers (xxxi). Reduction of the aryl nitro group and the olefin with catalytic Pd/C and hydrogen gas as described previously will afford the saturated aniline compounds (xxxii) which can be converted to a compound of the invention I by methods already described.

Scheme 8

Scheme 8 depicts the preparation of compounds of the invention I where X═OR$^1$. Compounds (xxvii), which can be purchased or readily prepared by one skilled in the art, can be treated with an allyl alcohol (xxviii) and a base, such as LiHMDS in a solvent such as THF to afford the alkyl ether (xxix). The allyl ether (xxix) can be encouraged to undergo a [3,3]-sigmatropic rearrangement by heating to high temperatures, for example 155° C. in a solvent such as diglyme to afford the phenolic compounds (xxx) with the allyl group transferred to the ortho position of the aryl ring. The phenol (xxx) can be treated sequentially with a base and an alkyl halide $R^1$—Z, where Z═Br or I in a solvent such as THF at room temperature or elevated temperatures to afford the aryl ethers (xxxi). Reduction of the aryl nitro group and the olefin with catalytic Pd/C and hydrogen gas as described previously will afford the saturated aniline compounds (xxxii) which can be converted to a compound of the invention I by methods previously described.

Scheme 8

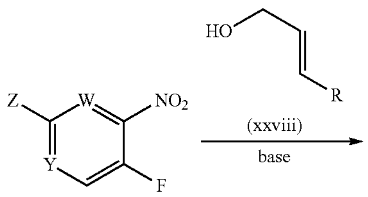

(xxvii)

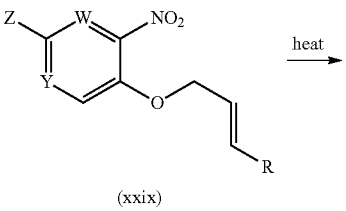

(xxix)

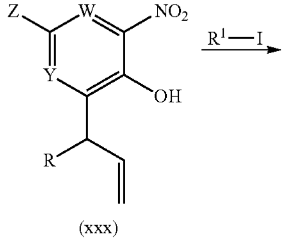

(xxx)

-continued

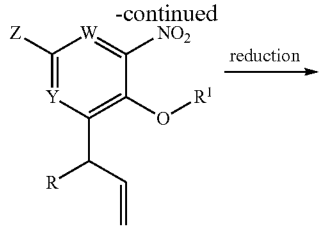

(xxxi)

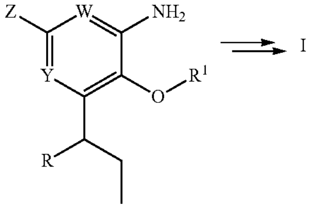

(xxxii)

In another embodiment depicted in Scheme 9, the aryl halides (i) can be treated with an alcohol $R^1$—OH in the presence of a base, such as BuLi in a solvent such as THF to afford the aryl ether (xxxiii). The aryl ethers (xxxiii) can be converted to compounds of the invention I by methods already described herein.

Scheme 9

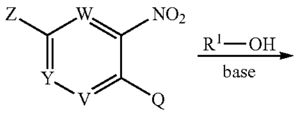

(i)

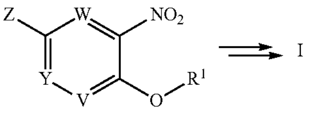

(xxxiii)

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS and Preparatory/Analytical HPLC Methods Employed in Characterization or Purification of Examples Analytical HPLC/MS was performed using the following methods:

Method A: Shimadzu SCL-10A liquid chromatographs and Waters MICROMASS® ZQ Mass Spectrometers (Desalvation Gas: Nitrogen; Desalvation Temp. 250° C.; Ion Source Temp: 120° C.; Positive Electrospray conditions) using the following method: Linear Gradient of 0% to 100% solvent B over 4 min; UV visualization at 220 nm; Column: Waters Sunfire C18 2.1 mm×30 mm; 2.5 um particle (Heated to Temp. 40° C.); Flow rate: 1 ml/min; Mobile phase A: 10%

MeOH, 90% Water, 0.1% TFA; Mobile phase B: 90% MeOH, 10% Water, 0.1% TFA;

Method B: Waters Acquity SDS using the following method: Linear Gradient of 2% to 98% solvent B over 1.6 min; UV visualization at 220 nm; Column: BEH C18 2.1 mm×50 mm; 1.7 um particle (Heated to Temp. 50° C.); Flow rate: 1 ml/min; Mobile phase A: 100% Water, 0.05% TFA; Mobile phase B: 100% Acetonitrile, 0.05% TFA;

Method C: Phenomenex-Luna C18 3 um 4.6x30 mm, 0% B-95% B with flow rate 4 mL/min and 2 min gradient time; Mobile phase A: 10% water/90% acetonitrile with 10 mM $NH_4OAc$; Mobile phase B: 10% water/90% acetonitrile with 10 mM $NH_4OAc$, wavelength 220 nM.

Method D: Phenomenex Luna C18, 2.0x30 mm, 5-μm particles; Mobile Phase A: 10:90 water:MeOH 0.1% TFA; Mobile Phase B: 10:90 water:MeOH 0.1% TFA; Temperature: RT; Gradient: 0-100% B over 2 minutes, then a 0.5-minute hold at 100% B; Flow: 1.5 mL/min.

Method E: YMC S5 ODS, 4.6x50 mm, 1.7-μm particles; Mobile Phase A: 10% MeOH-90% $H_2O$-0.2% $H_3PO_4$; Mobile Phase B: 90% MeOH-10% $H_2O$-0.2% $H_3PO_4$; Temperature: 40° C.; Gradient: 0-100% B over 4 minutes, then a 1-minute hold at 100% B; Flow: 4 mL/min.

Method F: Waters Acquity UPLC Column: BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

Preparatory chiral SFC chromatography was performed on a Thar 350 SFC chromatograph using the following method:

Method G: UV visualization at 220 nm; Column: Chiralpak AD-H SFC, 5x25 cm ID, 5 μm; Flow rate: 60.0 mL/min, 100 bar backpressure; Temperature: 40° C.; and Mobile Phase: 92/8, $CO_2$/MeOH.

Analytical chiral SFC chromatography was performed on a Berger Analytical parallel SFC chromatography using the following method:

Method H: UV visualization at 220 nm; Column: RR, Whelk-O1, 250×4.6 mm ID, 5 μm; Flow rate: 2 mL/min, 150 bar backpressure; and Mobile Phase: 80/20,$CO_2$/MeOH.

Method I (SFC): UV visualization at 220 nm; Column: AD, 250×4.6 mm ID, 5 μm; Flow rate: 3 mL/min, 100 bar backpressure; and Mobile Phase: 85/15, $CO_2$/MeOH.

NMR Employed in Characterization of Examples $^1H$ NMR spectra (unless otherwise noted) were obtained with JEOL or Bruker FOURIER® transform spectrometers operating at 400 MHz or 500 MHz. $^1H$-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1H$ NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Example 1

Enantiomer 1 and Enantiomer 2

3-(4-(diisobutylamino)-3-(3-(p-tolyl)ureido)phenyl)-2-methylpropanoic acid

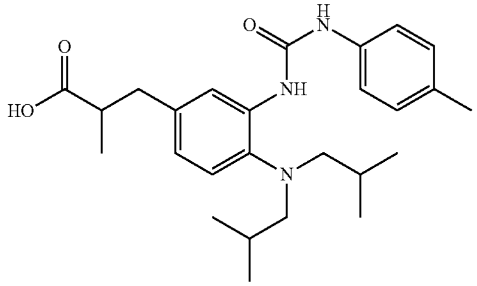 [SMILES: Cc1ccc(NC(=O)Nc2cc(CC(C)C(=O)O)ccc2N(CC(C)C)CC(C)C)cc1]

1A. 4-(diisobutylamino)-3-nitrobenzaldehyde

A suspension containing 4-fluoro-3-nitrobenzaldehyde (7.000 g, 41.4 mmol), cesium carbonate (20.23 g, 62.1 mmol) and diisobutylamine (16.05 g, 124 mmol) in DMF (70 mL) was heated to 100° C. for 1 h. After cooling to RT, the mixture was diluted with water and EtOAc. The layers were separated and the aqueous phase extracted with EtOAc (2×25 mL). The organic layers were combined, washed with water, brine, dried over $Na_2SO_4$, filtered and concentrated. Purification by flash chromatography gave 1A (orange solid, 10.79 g, 38.8 mmol, 94% yield). LC-MS Anal. Calc'd for $C_{15}H_{22}N_2O_3$ 278.16, found [M+H] 279.3. $T_r$=1.12 min (Method B). $^1H$ NMR (400 MHz, METHANOL-$d_4$) δ 9.79 (s, 1H), 8.25 (d, J=2.0 Hz, 1H), 7.93 (dd, J=8.9, 2.1 Hz, 1H), 7.40 (d, J=9.0 Hz, 1H), 3.14 (d, J=7.3 Hz, 4H), 2.02 (dt, J=13.4, 6.9 Hz, 2H), 0.97-0.78 (m, 12H)

1B. ethyl 3-(3-amino-4-(diisobutylamino)phenyl)-2-methylpropanoate

To a solution of sodium hydride (17.24 mg, 0.431 mmol) in 2 mL of THF at 0° C. was added ethyl 2-(diethoxyphosphoryl)propanoate (103 mg, 0.431 mmol) dropwise. The resulting suspension turned into a clear solution. After stirring at the same temperature for 10 min, a 2 mL THF solution of 1A (100 mg, 0.359 mmol) was added slowly and the resulting solution was warmed up to RT and stirred for 1 h. LC-MS showed product formation, it was diluted with EtOAc (10 mL) and water (10 mL). Aqueous layer was further extracted with EtOAc (2×10 mL), the combined extracts were washed with water, brine, dried over $MgSO_4$, filtered and concentrated. Purification via flash chromatography gave (E)-ethyl 3-(4-(diisobutylamino)-3-nitrophenyl)-2-methylacrylate (light yellow oil, 50 mg, 0.138 mmol, 38.4% yield). To a stirred solution of the (E)-ethyl 3-(4-(diisobutylamino)-3-nitrophenyl)-2-methylacrylate obtained above (50 mg, 0.138 mmol) in MeOH (4 mL) was added palladium on carbon (14.68 mg, 0.014 mmol) and the suspension was hydrogenated (1 atm, balloon) for 3 h. LC-MS indicated completion. The suspension was filtered through a pad of Celite and the filter cake was rinsed with EtOAc (20 mL). Combined filtrate and rinses were evaporated in vacuo to obtain 1B (light yellow oil, 25 mg, 0.07 mmol, 54% yield). 1B was used without purification in the next step. LC-MS Anal. Calc'd for $C_{20}H_{34}N_2O_2$ 334.26, found [M+H] 335.41. $T_r$=3.06 min (Method A). $^1H$ NMR (400 MHz, CHLOROFORM-d) δ 6.96 (d, J=7.9 Hz, 1H), 6.57-6.48 (m, 2H), 4.17-4.02 (m, 4H), 2.90 (dd, J=13.4, 6.8 Hz, 1H), 2.73-2.63 (m, 1H), 2.57 (d, J=7.3 Hz, 4H), 2.55-2.46 (m, 1H), 1.73 (dquin, J=13.5, 6.8 Hz, 2H), 1.19 (t, J=7.2 Hz, 3H), 1.14 (d, J=7.0 Hz, 3H), 0.90 (d, J=6.6 Hz, 12H)

1C. Racemic 3-(4-(diisobutylamino)-3-(3-(p-tolyl)ureido)phenyl)-2-methylpropanoic acid To a solution of 1B (25 mg, 0.075 mmol) in THF (1.5 mL) was added 1-isocyanato-4-methylbenzene (29.9 mg, 0.224 mmol). The resulting solution was stirred at rt for 2 h. The reaction mixture was concentrated and used without purification in the next step. The crude ester was dissolved in THF (1.500 mL) and Water (0.450 mL), then sodium hydroxide (0.224 mL, 0.224 mmol) was added. A solid precipitated. MeOH (~1 mL) was added. After 16 h, MeOH and THF were removed in vacuo and the crude material was diluted with 2 mL of water and the pH adjusted to ~4 using 1N HCl. The aqueous phase was then extracted with EtOAc (2×20 mL) and the combined organic phase was washed with brine, dried with $Na_2SO_4$ and concentrated to afford the title compound (32.6 mg, 0.074 mmol, 99% yield). LC-MS Anal. Calc'd for: $C_{26}H_{37}N_3O_3$ 439.28, found [M+H] 440.37. $T_r$=3.40 min (Method A). $^1H$ NMR (500 MHz, DMSO-$d_6$) δ 9.33 (s, 1H), 7.88-7.76 (m, 2H), 7.35 (d, J=8.4 Hz, 2H), 7.15-7.04 (m, 3H), 6.77 (dd, J=8.2, 1.7 Hz, 1H), 2.85 (dd, J=13.1, 6.7 Hz, 1H), 2.62 (d, J=6.9 Hz, 4H), 2.59-2.53 (m, 1H), 2.24 (s, 3H), 1.62 (dquin, J=13.4, 6.7 Hz, 2H), 1.03 (d, J=6.9 Hz, 3H), 0.83 (d, J=6.9 Hz, 12H)

Isomer 1 and isomer 2: 3-(4-(diisobutylamino)-3-(3-(p-tolyl)ureido)phenyl)-2-methylpropanoic acid Chiral separation of 1C gave 1D Enantiomer 1 and Enantiomer 2, absolute stereochemistry is unknown; Preparative chiral separation (Method G) of 1C gave 1D Enantiomer 1 and Enantiomer 2, absolute stereochemistry is unknown. Enantiomer 1: Chiral HPLC $T_r$=7.57 min (Method H); Enantiomer 1: LC-MS Anal. Calc'd for $C_{26}H_{37}N_3O_3$ 439.28, found [M+H] 440.36. $T_r$=3.43 min (Method A). $^1H$ NMR (400 MHz, CHLOROFORM-d) δ 8.17-8.04 (m, 2H), 7.24-7.16 (m, 2H), 7.15-7.07 (m, 2H), 7.01 (d, J=7.9 Hz, 1H), 6.96 (br. s., 1H), 6.78 (dd, J=8.0, 1.7 Hz, 1H), 3.01 (dd, J=13.1, 7.2 Hz, 1H), 2.79-2.71 (m, 1H), 2.70-2.61 (m, 1H), 2.53-2.41 (m, 4H), 2.32 (s, 3H), 1.59 (dquin, J=13.5, 6.8 Hz, 2H), 1.18 (d, J=6.8 Hz, 3H), 0.74 (dd, J=6.6, 3.5 Hz, 12H) Enantiomer 2: Chiral HPLC $T_r$=9.03 min (Method H); LC-MS Anal. Calc'd for $C_{26}H_{37}N_3O_3$ 439.28, found [M+H] 440.34. $T_r$=3.32 min (Method A). $^1H$ NMR (400 MHz, CHLOROFORM-d) δ 8.17-8.03 (m, 2H), 7.23-7.16 (m, 2H), 7.15-7.07 (m, 2H), 7.01 (d, J=8.1 Hz, 1H), 6.96 (br. s., 1H), 6.78 (dd, J=8.1, 1.5 Hz, 1H), 3.01 (dd, J=13.1, 7.4 Hz, 1H), 2.79-2.69 (m, 1H), 2.66 (d, J=13.2 Hz, 1H), 2.55-2.39 (m, 4H), 2.32 (s, 3H), 1.59 (dquin, J=13.4, 6.7 Hz, 2H), 1.18 (d, J=6.8 Hz, 3H), 0.74 (dd, J=6.6, 3.7 Hz, 12H).

Example 2

2-(3-(4-(diisobutylamino)-3-(3-(p-tolyl)ureido)phenyl)oxetan-3-yl)acetic acid

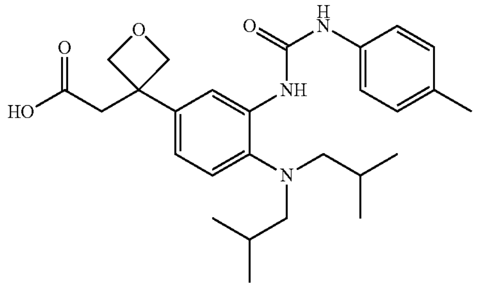 [SMILES: Cc1ccc(NC(=O)Nc2cc(C3(CC(=O)O)COC3)ccc2N(CC(C)C)CC(C)C)cc1]

2A. ethyl 2-(oxetan-3-ylidene)acetate

To a solution of oxetan-3-one (500 mg, 6.94 mmol) in $CH_2Cl_2$ (14 mL) at 0° C. was added ethyl 2-(triphenylphosphoranylidene)acetate (2659 mg, 7.63 mmol). The reaction mixture was allowed to warm to RT and stirred for 2 h. LC-MS indicated the desired peak. The reaction mixture was then quenched with water (5 mL), extracted with $CH_2Cl_2$ (2×10 mL). The combined organic extracts were washed with water, brine, dried over $MgSO_4$, filtered and concentrated. Purification via flash chromatography gave 2A (colorless oil, 800 mg, 5.63 mmol, 81% yield). LC-MS Anal. Calc'd for $C_7H_{10}O_3$ 142.06, found [M+H] 143.11. $T_r$=1.65 min (Method B). $^1H$ NMR (400 MHz, CHLOROFORM-d) δ 5.62 (quin, J=2.4 Hz, 1H), 5.54-5.44 (m, 2H), 5.29 (td, J=3.5, 2.2 Hz, 2H), 4.15 (q, J=7.1 Hz, 2H), 1.26 (t, J=7.2 Hz, 3H)

2B. ethyl 2-(3-(4-fluoro-3-nitrophenyl)oxetan-3-yl)acetate

To a solution of $[Rh(COD)_2Cl]_2$ (26.0 mg, 0.053 mmol) in 1,4-dioxane (5 mL) was added potassium hydroxide (0.915 mL, 1.372 mmol) followed by 2A (150 mg, 1.055 mmol) (rinsed with 1 mL 1,4-dioxane) and a solution of (4-fluoro-3-nitrophenyl)boronic acid (293 mg, 1.583 mmol) in 1,4-dioxane (1.000 mL). After addition of potassium hydroxide, the solution turned into a yellow suspension. After addition of oxetane, it turned into a clear brown solution. After stirring at RT for 12 h, LC-MS showed a new peak. Heated at 50° C. for 2 h, no change. After cooling to RT, it was diluted with 5 mL of brine and 10 mL of EtOAc. The aqueous layer was further extracted with EtOAc (3×10 mL) and the combined organic extracts were washed with water, brine, dried over $MgSO_4$, filtered and concentrated. Purification via flash chromatography gave 2B (yellow solid, 30 mg, 0.106 mmol, 10.04% yield). LC-MS Anal. Calc'd for $C_{13}H_{14}FNO_5$ 283.09, did not show parent ion in MS, $T_r$=2.48 min (Method A). $^1H$ NMR (400 MHz, CHLOROFORM-d) δ 7.90 (dd, J=6.9, 2.5 Hz, 1H), 7.55 (ddd, J=8.6, 4.1, 2.4 Hz, 1H), 7.30 (dd, J=10.3, 8.6 Hz, 1H), 4.96 (d, J=6.4 Hz, 2H), 4.88 (d, J=6.6 Hz, 2H), 4.05 (q, J=7.0 Hz, 2H), 3.18 (s, 2H), 1.18 (t, J=7.2 Hz, 3H)

2C. ethyl 2-(3-(4-(diisobutylamino)-3-nitrophenyl)oxetan-3-yl)acetate

To a flask containing 2B (30 mg, 0.106 mmol) in DMF (1 mL) was added diisobutylamine (110 mg, 0.847 mmol) and cesium carbonate (41.4 mg, 0.127 mmol). The reaction mixture was heated at 100° C. for 3 h. LC-MS indicated the desired peak. Then it was heated at 110° C. for 4 h. LC-MS indicated completion. After cooling to RT, it was diluted with EtOAc (20 mL) and water (10 mL). Aqueous layer was further extracted with EtOAc (3×10 mL), the combined extracts were washed with water, brine, dried over $MgSO_4$, filtered and concentrated. Purification via flash chromatography gave 2C (yellow oil, 18 mg, 0.046 mmol, 43.3% yield). LC-MS Anal. Calc'd for $C_{21}H_{32}N_2O_5$ 392.23, found [M+H] 393.23. $T_r$=3.79 min (Method A). $^1H$ NMR (400 MHz, CHLOROFORM-d) δ 7.52 (d, J=2.4 Hz, 1H), 7.30-7.23 (m, 1H), 7.10 (d, J=8.8 Hz, 1H), 4.95 (d, J=6.2 Hz, 2H), 4.85 (d, J=6.2 Hz, 2H), 4.04 (q, J=7.0 Hz, 2H), 3.10 (s, 2H), 2.92 (d, J=7.3 Hz, 4H), 1.90 (dquin, J=13.5, 6.8 Hz, 2H), 1.14 (t, J=7.2 Hz, 3H), 0.84 (d, J=6.6 Hz, 12H)

2-(3-(4-(diisobutylamino)-3-(3-(p-tolyl)ureido)phenyl)oxetan-3-yl)acetic acid

To a stirred solution of 2C (18 mg, 0.046 mmol) in ethyl acetate (2.00 mL) was added palladium on carbon (9.76 mg, 9.17 μmol) and the suspension was hydrogenated (1 atm, balloon) for 1 hour. The suspension was then filtered through a pad of Celite. The filter cake was rinsed with EtOAc (2×) and the combined filtrate and rinses were evaporated in vacuo. To this crude aniline solution in THF (2 mL) was added 1-isocyanato-4-methylbenzene (9.16 mg, 0.069 mmol). The resulting solution was stirred at rt for 3 hours. The reaction mixture was concentrated and used without purification in the next step. The crude ester was dissolved in THF (1.000 mL) and Water (0.500 mL) then sodium hydroxide (1M solution, 0.138 mL, 0.138 mmol) was added. A precipitate formed, then MeOH (~1 mL) was added. After 16 hours, the MeOH and THF were removed in vacuo and the crude was diluted with 2 mL of water. The pH was adjusted to ~4 using 1N HCl. The aqueous phase was then extracted with EtOAc (3×) and the combined organic phase was washed with brine, dried with $Na_2SO_4$ and concentrated. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to afford the title compound (14.4 mg, 0.027 mmol, 58% yield). LC-MS Anal. Calc'd for $C_{27}H_{37}N_3O_4$ 467.28, found [M+H] 468.25. $T_r$=3.34 min (Method A). $^1H$ NMR (400 MHz, CHLOROFORM-d) δ 7.41-7.33 (m, 3H), 7.32-7.20 (m, 2H), 7.12 (d, J=7.9 Hz, 2H), 5.00-4.85 (m, 4H), 3.24 (d, J=6.6 Hz, 4H), 3.13 (s, 2H), 2.38-2.27 (m, 3H), 2.15-2.02 (m, 2H), 1.05 (d, J=5.9 Hz, 12H)

Example 3

Racemic 3-(4-(diisobutylamino)-3-(3-(p-tolyl)ureido)phenyl) butanoic acid

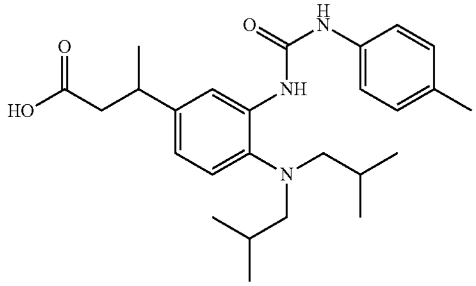 [SMILES: Cc1ccc(NC(=O)Nc2cc(C(C)CC(=O)O)ccc2N(CC(C)C)CC(C)C)cc1]

3A. 1-(4-(diisobutylamino)-3-nitrophenyl)ethanone

To a flask containing 1-(4-fluoro-3-nitrophenyl)ethanone (1.700 g, 9.28 mmol) in DMF (30 mL) was added diisobutylamine (1 g, 7.74 mmol) and cesium carbonate (3.03 g, 9.28 mmol). The reaction mixture was heated at 100° C. for 3 h. LC-MS indicated product formation. After cooling to RT, it was diluted with EtOAc (20 mL) and water (10 mL). Aqueous layer was further extracted with EtOAc (2×20 mL), the combined extracts were washed with water, brine, dried over $MgSO_4$, filtered and concentrated. Purification via flash chromatography gave 3A (oragne oil, 1.6 g, 5.47 mmol, 70.7% yield). LC-MS Anal. Calc'd for $C_{16}H_{24}N_2O_3$ 292.18, found [M+H] 293.25. $T_r$=3.65 min (Method A). $^1$H NMR (400 MHz, CHLOROFORM-d) δ 8.34 (d, J=2.2 Hz, 1H), 7.96 (dd, J=9.0, 2.2 Hz, 1H), 7.10 (d, J=9.0 Hz, 1H), 3.03 (d, J=7.3 Hz, 4H), 2.55 (s, 3H), 1.98 (dquin, J=13.5, 6.8 Hz, 2H), 0.86 (d, J=6.6 Hz, 12H)

3B. E and Z isomers of ethyl 3-(4-(diisobutylamino)-3-nitrophenyl)but-2-enoate

To a solution of NaH (0.482 g, 12.04 mmol) in THF (40 mL) at 0° C. was added added ethyl 2-(diethoxyphosphoryl) acetate (2.191 mL, 10.94 mmol). After stirring for 30 min, a solution of 3A (2.191 mL, 10.94 mmol) in THF (10 mL) was added. After stirring at RT for 36 h. LC-MS indicated 1.5:1 starting material and desired product. Heated the reaction mixture at 50° C. for 12 h, ratio changed to 1:1 but stopped changing. After cooling to RT, it was quenched with 10 mL saturated aqueous $NH_4Cl$. The aqueous layer was further extracted with EtOAc (3×20 mL) and the combined organic extracts were washed with water, brine, dried over $MgSO_4$, filtered and concentrated. Purification via flash chromatography gave E isomer of 3B (orange oil, 0.4 g, 1.104 mmol, 20.17% yield) and Z isomer of 3B (orange oil, 0.03 g, 0.083 mmol, 1.512% yield). LC-MS Anal. Calc'd for $C_{20}H_{30}N_2O_4$ 362.22, found [M+H] 363.22. $T_r$=4.03 min (E) and 4.24 min (Z) (Method A). Major E isomer: $^1$H NMR (400 MHz, CHLOROFORM-d) δ 7.90 (d, J=2.4 Hz, 1H), 7.53 (dd, J=8.8, 2.4 Hz, 1H), 7.08 (d, J=9.0 Hz, 1H), 6.14 (d, J=1.3 Hz, 1H), 4.22 (q, J=7.1 Hz, 2H), 2.98 (d, J=7.3 Hz, 4H), 2.56 (d, J=1.1 Hz, 3H), 2.01-1.89 (m, 2H), 1.33 (t, J=7.2 Hz, 3H), 0.85 (d, J=6.6 Hz, 12H) Minor Z isomer: $^1$H NMR (400 MHz, CHLOROFORM-d) δ 7.67 (d, J=2.2 Hz, 1H), 7.32 (dd, J=8.7, 2.3 Hz, 1H), 7.05 (d, J=8.8 Hz, 1H), 5.90 (d, J=1.5 Hz, 1H), 4.06 (q, J=7.1 Hz, 2H), 2.95 (d, J=7.3 Hz, 4H), 2.18 (d, J=1.5 Hz, 3H), 1.94 (dt, J=13.5, 6.8 Hz, 2H), 1.14 (t, J=7.0 Hz, 3H), 0.91-0.80 (m, 12H)

3C. ethyl 3-(3-amino-4-(diisobutylamino)phenyl)butanoate

To a stirred solution of the E isomer 3B (200 mg, 0.552 mmol) in ethyl acetate (10 mL) was added palladium on carbon (58.7 mg, 0.055 mmol) and the suspension was hydrogenated (1 atm, balloon) for 2 h. LC-MS indicated completion. The suspension was filtered through a pad of Celite and the filter cake was rinsed with EtOAc (3×20 mL). Combined filtrate and rinses were concentrated in vacuo. Purification via flash chromatography gave 3C (light yellow oil, 140 mg, 0.419 mmol, 76% yield). LC-MS Anal. Calc'd for $C_{20}H_{34}N_2O_2$ 334.26, found [M+H] 335.31. $T_r$=3.09 min (Method A). $^1$H NMR (400 MHz, CHLOROFORM-d) δ 6.98 (d, J=7.9 Hz, 1H), 6.62-6.51 (m, 2H), 4.09 (q, J=7.3 Hz, 4H) (2 proton from $NH_2$), 3.20-3.08 (m, 1H), 2.63-2.52 (m, 5H), 2.51-2.40 (m, 1H), 1.73 (dquin, J=13.5, 6.8 Hz, 2H), 1.26 (d, J=7.0 Hz, 3H), 1.18 (t, J=7.2 Hz, 3H), 0.90 (d, J=6.6 Hz, 12H)

3-(4-(diisobutylamino)-3-(3-(p-tolyl)ureido)phenyl) butanoic acid

To a solution of 3C (70 mg, 0.209 mmol) in THF (2 mL) was added 1-isocyanato-4-methylbenzene (41.8 mg, 0.314 mmol). The resulting solution was stirred at rt for 1 h. The reaction mixture was concentrated and used without purification in the next step. The crude ester was dissolved in THF (2 mL) and Water (1 mL), then sodium hydroxide (0.628 mL, 0.628 mmol) was added. A precipitate formed, then MeOH (~1 mL) was added. After 20 h, most of the MeOH and THF were removed in vacuo and the crude was diluted with 2 mL of water. The pH was adjusted to ~4 using 1N HCl. The aqueous phase was then extracted with EtOAc (3×) and the combined organic phase was washed with brine, dried with $Na_2SO_4$ and concentrated. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 55-95% B over 25 minutes, then a 15-minute hold at 100% B; Flow: 20 mL/min. Fractions containing the desired product were combined and dried via centrifugal evaporation to afford the title compound (65.4 mg, 0.149 mmol, 71% yield). LC-MS Anal. Calc'd for $C_{26}H_{37}N_3O_3$ 439.28, found [M+H] 440.32. $T_r$=3.41 min (Method A). $^1$H NMR (500 MHz, DMSO-$d_6$) δ 9.32 (s, 1H), 7.88-7.79 (m, 2H), 7.35 (d, J=8.4 Hz, 2H), 7.09 (dd, J=16.1, 8.2 Hz, 3H), 6.83 (dd, J=8.4, 2.0 Hz, 1H), 3.10-3.02 (m, 1H), 2.61 (d, J=6.9 Hz, 4H), 2.44-2.34 (m, 2H), 2.24 (s, 3H), 1.68-1.53 (m, 2H), 1.18 (d, J=6.9 Hz, 3H), 0.84 (d, J=6.4 Hz, 12H).

Example 4

Enantiomer 1 and Enantiomer 2

3-(4-(diisobutylamino)-3-(3-(2-fluorophenyl)ureido)phenyl)butanoic acid

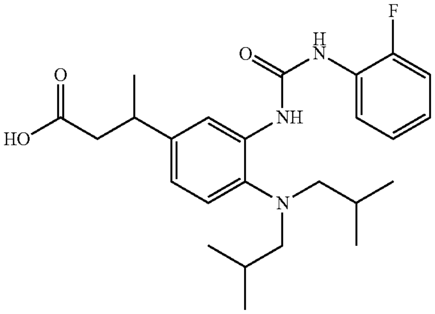 [SMILES: CC(C)CN(CC(C)C)c1ccc(C(C)CC(=O)O)cc1NC(=O)Nc1ccccc1F]

Racemic example 4 was obtained following the same procedure of Example 3 utilizing 2-fluoroaniline for urea formation. Enantiomer 1 and Enantiomer 2 were obtained by chiral HPLC (Method G), absolute stereochemistry unknown. Enantiomer 1: Analytical Chiral HPLC Tr=5.642 min (Method H); LC-MS Anal. Calc'd for $C_{25}H_{34}FN_3O_3$ 443.26, found [M+H] 444.16. $T_r$=3.32 min (Method A). $^1$H NMR (400 MHz, CHLOROFORM-d) δ 8.36 (s, 1H), 8.16-8.05 (m, 2H), 7.18-6.97 (m, 4H), 6.88 (dd, J=8.1, 2.2 Hz, 1H), 6.54 (d, J=3.3 Hz, 1H), 3.34-3.20 (m, 1H), 2.75-2.65 (m, 1H), 2.64-2.53 (m, 5H), 1.72 (dquin, J=13.5, 6.8 Hz, 2H), 1.35 (d, J=6.8 Hz, 3H), 0.91 (d, J=6.6 Hz, 12H); Enantiomer 2: Analytical Chiral HPLC Tr=6.293 min (Method H); LC-MS Anal. Calc'd for $C_{25}H_{34}FN_3O_3$ 443.26, found [M+H] 444.17. $T_r$=3.30 min (Method A). $^1$H NMR (400 MHz, CHLOROFORM-d) δ 8.36 (s, 1H), 8.18-8.04 (m, 2H), 7.21-6.97 (m, 4H), 6.88 (dd, J=8.1, 2.0 Hz, 1H), 6.55 (d, J=2.9 Hz, 1H), 3.35-3.19 (m, 1H), 2.76-2.64 (m, 1H), 2.64-2.52 (m, 5H), 1.72 (dquin, J=13.4, 6.8 Hz, 2H), 1.34 (d, J=6.8 Hz, 3H), 0.91 (d, J=6.6 Hz, 12H)

Example 5

Racemic 3-(3-(3-(4-chloro-2-fluorophenyl)ureido)-4-(diisobutylamino)phenyl)butanoic acid

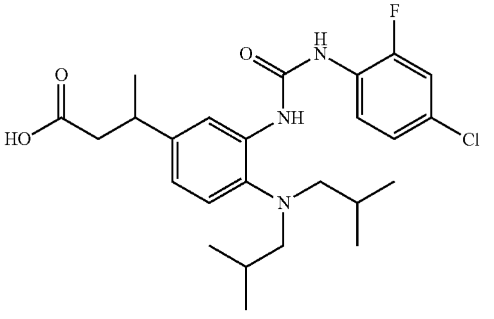 [SMILES: CC(C)CN(CC(C)C)c1ccc(C(C)CC(=O)O)cc1NC(=O)Nc1ccc(Cl)cc1F]

Example 5 was obtained following the same procedure of Example 3 utilizing 3-fluoro-4-chloroaniline in the urea formation. LC-MS Anal. Calc'd for $C_{25}H_{33}ClFN_3O_3$ 477.22, found [M+H] 478.17. $T_r$=3.63 min (Method A). $^1$H NMR (500 MHz, DMSO-$d_6$) δ 9.44 (s, 1H), 8.12 (s, 1H), 8.06 (t, J=8.9 Hz, 1H), 7.75 (d, J=2.5 Hz, 1H), 7.45 (dd, J=10.9, 2.5 Hz, 1H), 7.26-7.18 (m, 1H), 7.14-7.06 (m, 1H), 6.87 (dd, J=8.4, 2.0 Hz, 1H), 3.11-3.01 (m, 1H), 2.64 (d, J=6.9 Hz, 4H), 2.48-2.37 (m, 2H), 1.64 (dquin, J=13.2, 6.7 Hz, 2H), 1.18 (d, J=6.9 Hz, 3H), 0.83 (d, J=6.4 Hz, 12H)

Example 6

Racemic 3-(4-(diisobutylamino)-3-(3-(4-ethoxyphenyl)ureido)phenyl)butanoic acid

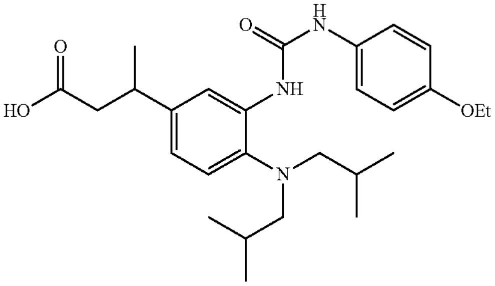 [SMILES: CCOc1ccc(NC(=O)Nc2cc(C(C)CC(=O)O)ccc2N(CC(C)C)CC(C)C)cc1]

Example 6 was obtained following the same procedure of Example 3 utilizing 4-ethoxyaniline in the urea formation. LC-MS Anal. Calc'd for $C_{27}H_{39}N_3O_4$ 469.29, found [M+H] 470.24. $T_r$=3.41 min (Method A). $^1$H NMR (500 MHz, DMSO-$d_6$) δ 9.21 (s, 1H), 7.95 (s, 1H), 7.87 (d, J=2.0 Hz, 1H), 7.43-7.29 (m, 2H), 7.11 (d, J=8.4 Hz, 1H), 6.90-6.74 (m, 3H), 3.97 (q, J=6.9 Hz, 2H), 3.12-2.99 (m, 1H), 2.60 (d, J=6.9 Hz, 4H), 2.48-2.35 (m, 2H), 1.68-1.53 (m, 2H), 1.31 (t, J=7.2 Hz, 3H), 1.18 (d, J=6.9 Hz, 3H), 0.84 (d, J=6.9 Hz, 12H)

Example 7

3-(4-(diisobutylamino)-3-(3-(6-methylpyridin-3-yl)ureido)phenyl)butanoic acid

Racemic

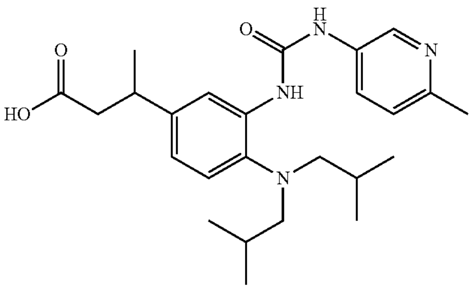 [SMILES: Cc1ccc(NC(=O)Nc2cc(C(C)CC(=O)O)ccc2N(CC(C)C)CC(C)C)cn1]

Example 7 was obtained following the same procedure of example 3 except for the urea formation step: To a solution of triphosgene (89 mg, 0.299 mmol) in THF (2 mL) was added 6-methylpyridin-3-amine (81 mg, 0.747 mmol) and Hunig's Base (0.261 mL, 1.495 mmol). After stirring for 1 h, ethyl 3-(3-amino-4-(diisobutylamino)phenyl)butanoate (50 mg, 0.149 mmol) in THF (2.000 mL) was added. The resulting solution was stirred at RT for 1 h. After removing solvent in vacuo, the crude ester was dissolved in THF (1.000 mL) and water (0.200 mL) then 1N aqueous sodium hydroxide (0.448 mL, 0.448 mmol) was added. MeOH (1 mL) was added to dissolve the precipitate and it turned into a clear yellow solution. After 48 h, reaction was complete by LC-MS. Most MeOH and THF was removed in vacuo and the crude was diluted with 2 mL of water, the pH was adjusted to ca. 6 using 1N aqueous HCl. The aqueous phase was then extracted with EtOAc (3×10 mL) and the combined organic extracts were washed with brine, dried over $Na_2SO_4$, filtered and concentrated. Preparative HPLC gave example 7 (light yellow oil, 43 mg, 0.097 mmol, 65% yield). LC-MS Anal. Calc'd for $C_{25}H_{36}N_4O_3$ 440.28, found [M+H] 441.19. $T_r$=2.83 min (Method A). $^1$H NMR (500 MHz, DMSO-$d_6$) δ 8.47 (d, J=2.0 Hz, 1H), 7.89-7.80 (m, 2H), 7.15 (dd, J=14.9, 8.4 Hz, 2H), 6.85 (dd, J=7.9, 2.0 Hz, 1H), 3.11-3.03 (m, 1H), 2.63 (d, J=6.9 Hz, 4H), 2.48-2.41 (m, 2H), 2.40 (s, 3H), 1.62 (dquin, J=13.4, 6.7 Hz, 2H), 1.19 (d, J=6.9 Hz, 3H), 0.85 (d, J=6.4 Hz, 12H)

Example 8

3-(4-((4-chlorobenzyl)(2-methoxyethyl)amino)-3-(3-(p-tolyl)ureido)phenyl)butanoic acid Racemic

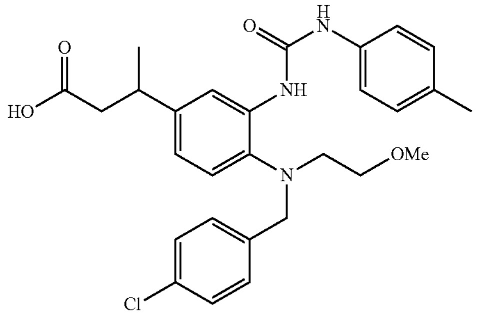 [SMILES: COCCN(Cc1ccc(Cl)cc1)c1ccc(C(C)CC(=O)O)cc1NC(=O)Nc1ccc(C)cc1]

To a solution of NaH (0.480 g, 12.01 mmol) in THF (40 mL) at 0° C. was added ethyl 2-(diethoxyphosphoryl)acetate (2.186 mL, 10.92 mmol). After stirring for 2 h, a solution of 1-(4-fluoro-3-nitrophenyl)ethanone (2.19 mL, 10.92 mmol) in THF (10 mL) was added. The resulting solution was slowly warmed up to RT and stirred for 20 h. LC-MS indicated desired product. It was quenched with saturated aqueous $NH_4Cl$. The aqueous layer was further extracted with EtOAc (3×20 mL) and the combined organic extracts were washed with water, brine, dried over $MgSO_4$, filtered and concentrated. Purification via flash chromatography gave ethyl 3-(4-fluoro-3-nitrophenyl)but-2-enoate (orange oil, 700 mg, 2.76 mmol, 50.6% yield), To a flask containing above obtained ethyl 3-(4-fluoro-3-nitrophenyl)but-2-enoate (300 mg, 1.185 mmol) in DMF (10 mL) was added N-(4-chlorobenzyl)-2-methoxyethanamine hydrochloride (308 mg, 1.303 mmol) and cesium carbonate (463 mg, 1.422 mmol). The reaction mixture was heated at 100° C. for 16 h. After cooling to RT, it was diluted with EtOAc (20 mL) and water (10 mL). Aqueous layer was further extracted with EtOAc (3×20 mL), the combined extracts were washed with water, brine, dried over $MgSO_4$, filtered and concentrated. Purification via flash chromatography gave ethyl 3-(4-((4-chlorobenzyl)(2-methoxyethyl)amino)-3-nitrophenyl)but-2-enoate (yellow oil, 200 mg, 0.462 mmol, 39.0% yield). To a stirred solution of the above obtained ethyl 3-(4-((4-chlorobenzyl)(2-methoxyethyl)amino)-3-nitrophenyl)but-2-enoate (200 mg, 0.462 mmol) in ethyl acetate (10 mL) was added palladium on carbon (49.2 mg, 0.046 mmol) and the suspension was hydrogenated (1 atm, balloon) for 1 h. The suspension was filtered through a pad of Celite and the filter cake was rinsed with EtOAc (3×20 mL). Combined filtrate and rinses were concentrated in vacuo. Purification via flash chromatography gave ethyl 3-(3-amino-4-((4-chlorobenzyl)(2-methoxyethyl)amino)phenyl)butanoate (yellow oil, 120 mg, 0.296 mmol, 64.1% yield). To a solution of ethyl 3-(3-amino-4-((4-chlorobenzyl)(2-methoxyethyl)amino)phenyl)butanoate obtained above (120 mg, 0.296 mmol) in THF (8 mL) was added 1-isocyanato-4-methylbenzene (59.2 mg, 0.445 mmol). The resulting solution was stirred at RT for 2 h. The reaction mixture was concentrated. Purification via flash chromatography gave 12 mg urea product. This ester was dissolved in THF (2.000 mL) and water (1.000 mL) then 1N aqueous sodium hydroxide (0.889 mL, 0.889 mmol) was added. MeOH (2 mL) was added to dissolve the precipitate and it turned into a clear yellow solution. After 24 h, reaction was complete by LC-MS. Most MeOH and THF was removed in vacuo and the crude was diluted with 2 mL of water, the pH was adjusted to ca.4 using 1N aqueous HCl. The aqueous phase was then extracted with EtOAc (3×10 mL) and the combined organic extracts were washed with brine, dried over $Na_2SO_4$ and concentrated. Preparative HPLC gave example 8 (light yellow oil, 2.5 mg, 0.0049 mmol, 1.7% yield). LC-MS Anal. Calc'd for $C_{28}H_{32}ClN_3O_4$ 509.21, found [M+H] 510.16. $T_r$=3.69 min (Method A). $^1$H NMR (500 MHz, DMSO-$d_6$) δ 8.30 (d, J=1.0 Hz, 2H), 7.94 (s, 1H), 7.39 (d, J=8.4 Hz, 2H), 7.35-7.30 (m, 2H), 7.29-7.22 (m, 2H), 7.09 (d, J=7.9 Hz, 3H), 6.74 (dd, J=8.4, 2.0 Hz, 1H), 3.17 (s, 3H), 3.07-2.95 (m, 4H), 2.40-2.26 (m, 2H), 2.25 (s, 3H), 1.13 (d, J=6.4 Hz, 3H) (some peaks buried under DMSO)

Example 9

3-(3-(3-(2-fluorophenyl)ureido)-4-(1-phenylpropoxy)phenyl)butanoic acid

Racemic Mixture of Diastereomers

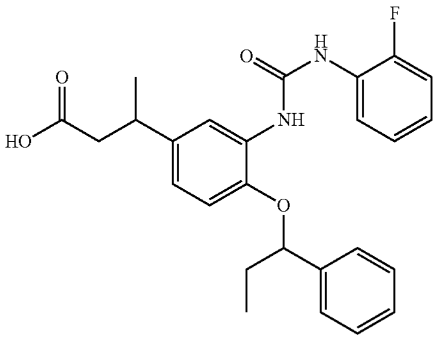 [SMILES: CCC(Oc1ccc(C(C)CC(=O)O)cc1NC(=O)Nc1ccccc1F)c1ccccc1]

9A. 1-(3-nitro-4-(1-phenylpropoxy)phenyl)ethanone

To a solution of triphenylphosphine (1086 mg, 4.14 mmol) in THF (10 mL) was added DIAD (0.805 mL, 4.14 mmol). The reaction mixture was stirred for 10 min. Then a solution of 1-(4-hydroxy-3-nitrophenyl)ethanone (500 mg, 2.76 mmol) and 1-phenylpropan-1-ol (376 mg, 2.76 mmol) in THF (10.00 mL) was added dropwise. The reaction mixture was then stirred at RT for 3 h. It was then diluted with EtOAc (20 mL) and water (10 mL). The aqueous layer was extracted with EtOAc (2×20 mL) and the combined organic extracts were washed with water, brine, dried over $Na_2SO_4$, filtered and concentrated. Purification via flash chromatography gave the 9A (light yellow oil, 600 mg, 2.005 mmol, 72.6% yield). LC-MS Anal. Calc'd for $C_{17}H_{17}NO_4$ 299.12, found mass of phenol 252.09; $T_r$=3.41 min (Method A). $^1H$ NMR (400 MHz, CHLOROFORM-d) δ 8.37 (d, J=2.2 Hz, 1H), 7.93 (dd, J=9.0, 2.2 Hz, 1H), 7.40-7.34 (m, 4H), 7.33-7.28 (m, 1H), 6.94 (d, J=9.0 Hz, 1H), 5.28 (dd, J=7.0, 5.5 Hz, 1H), 2.54 (s, 3H), 2.18-2.04 (m, 1H), 2.04-1.91 (m, 1H), 1.03 (t, J=7.4 Hz, 3H)

9B. ethyl 3-(3-amino-4-(1-phenylpropoxy)phenyl) butanoate (racemic)

To a solution of NaH (176 mg, 4.41 mmol) in THF (8 mL) at 0° C. was added ethyl 2-(diethoxyphosphoryl)acetate (0.802 mL, 4.01 mmol). After 15 min, it became a clear solution. Then 9A (600 mg, 2.005 mmol) in THF (4.00 mL) was added. After stirring at RT for 4 h. LC-MS indicated product formation, it was quenched with 10 mL of saturated aqueous $NH_4Cl$. The aqueous layer was further extracted with EtOAc (3×20 mL) and the combined organic extracts were washed with water, brine, dried over $MgSO_4$, filtered and concentrated. Purification via flash chromatography gave an inseparable mixture of E and Z ethyl 3-(3-nitro-4-(1-phenylpropoxy)phenyl)but-2-enoate (yellow oil, 580 mg, 1.570 mmol, 78% yield). To a stirred solution of the above obtained mixture (340 mg, 0.920 mmol) in ethyl acetate (12 mL) was added palladium on carbon (98 mg, 0.092 mmol) and the suspension was hydrogenated (1 atm, balloon) for 1 h. The suspension was filtered through a pad of Celite and the filter cake was rinsed with EtOAc (3×20 mL). Combined filtrate and rinses were concentrated in vacuo. Purification via flash chromatography gave 9B (yellow oil, 120 mg, 0.351 mmol, 38.2% yield). LC-MS Anal. Calc'd for $C_{21}H_{27}NO_3$ 341.20, found [M+H] 342.24. $T_r$=2.85 min (Method A). $^1H$ NMR (400 MHz, CHLOROFORM-d) δ 7.43-7.32 (m, 3H), 7.32-7.23 (m, 1H), 6.60 (d, J=2.2 Hz, 1H), 6.53 (d, J=8.4 Hz, 1H), 6.41 (dd, J=8.4, 2.0 Hz, 1H), 5.02 (dd, J=7.0, 5.7 Hz, 1H), 4.09 (qd, J=7.2, 3.2 Hz, 2H), 3.88 (br. s., 2H), 3.18-3.05 (m, 1H), 2.60-2.37 (m, 2H), 2.13-1.85 (m, 2H), 1.23 (d, J=6.8 Hz, 3H), 1.19 (td, J=7.2, 4.0 Hz, 3H), 1.03 (t, J=7.5 Hz, 3H)

3-(3-(3-(2-fluorophenyl)ureido)-4-(1-phenylpropoxy)phenyl)butanoic acid

Racemic Mixture of Diastereomers

To a solution of 9B (15 mg, 0.044 mmol) in THF (2 mL) was added 1-fluoro-2-isocyanatobenzene (9.04 mg, 0.066 mmol). The resulting solution was stirred at rt for 1 h. The reaction mixture was concentrated and the crude ester was dissolved in THF (2 mL) and Water (1 mL) then sodium hydroxide (0.132 mL, 0.132 mmol) was added. A precipitate formed, then MeOH (~1 mL) was added. After 20 h, most of the MeOH and THF was removed in vacuo and the crude was diluted with 5 mL of water. The pH was adjusted to ~4 using 1N HCl. The aqueous phase was then extracted with EtOAc (3×) and the combined organic phase was washed with brine, dried with $Na_2SO_4$ and concentrated. The crude material was purified via preparative HPLC with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 25-100% B over 15 minutes, then a 5-minute hold at 100% B; Flow: 20 mL/min. Fractions containing the desired product were combined and dried via centrifugal evaporation to afford the title compound (15.2 mg, 0.034 mmol, 77% yield). LC-MS Anal. Calc'd for $C_{26}H_{27}FN_2O_4$ 450.20, found [M+H] 451.07. $T_r$=3.63 min (Method A). $^1H$ NMR (500 MHz, DMSO-$d_6$) δ 9.39 (d, J=1.5 Hz, 1H), 8.63-8.50 (m, 1H), 8.24-8.10 (m, 1H), 7.97 (t, J=2.0 Hz, 1H), 7.43 (d, J=6.9 Hz, 2H), 7.34 (t, J=7.7 Hz, 2H), 7.30-7.21 (m, 2H), 7.18-7.11 (m, 1H), 7.07-6.97 (m, 1H), 6.74 (dd, J=8.4, 3.0 Hz, 1H), 6.66 (dt, J=8.4, 2.5 Hz, 1H), 5.26 (dd, J=7.4, 5.9 Hz, 1H), 2.98 (sxt, J=7.1 Hz, 1H), 2.44-2.31 (m, 2H), 2.06 (dquin, J=14.2, 7.2 Hz, 1H), 1.92-1.80 (m, 1H), 1.12 (d, J=6.4 Hz, 3H), 0.97 (t, J=7.2 Hz, 3H).

Example 10

Racemic Mixture of Diastereomers 3-(4-(1-phenylpropoxy)-3-(3-(p-tolyl)ureido)phenyl) butanoic acid

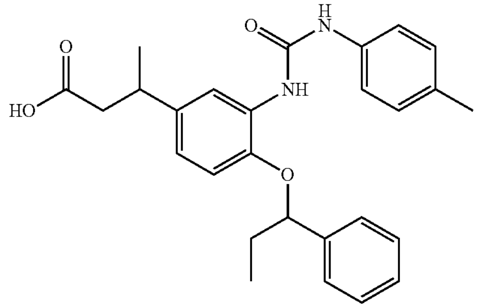 [SMILES: CCC(Oc1ccc(C(C)CC(=O)O)cc1NC(=O)Nc1ccc(C)cc1)c1ccccc1]

Example 10 was obtained following the same procedure in Example 9 utilizing para-toluylisocyanante in the urea formation. LC-MS Anal. Calc'd for $C_{27}H_{30}N_2O_4$ 446.22, found [M+H] 447.12. $T_r$=3.70 min (Method A). $^1H$ NMR (500 MHz, DMSO-$d_6$) δ 9.42 (s, 1H), 8.07 (s, 1H), 8.00 (t, J=2.0 Hz, 1H), 7.41 (dd, J=16.6, 7.7 Hz, 4H), 7.34 (t, J=7.4 Hz, 2H), 7.29-7.21 (m, 1H), 7.11 (d, J=8.4 Hz, 2H), 6.73 (dd, J=8.4, 3.0 Hz, 1H), 6.62 (dt, J=8.4, 2.5 Hz, 1H), 5.26 (dd, J=7.2, 5.7 Hz, 1H), 2.98 (sxt, J=7.1 Hz, 1H), 2.40-2.31 (m, 2H), 2.26 (s, 3H), 2.12-1.99 (m, 1H), 1.92-1.78 (m, 1H), 1.11 (d, J=6.9 Hz, 3H), 0.97 (t, J=7.4 Hz, 3H)

Example 11

Racemic Mixture of Diastereomers 3-(4-(cyclopropyl(phenyl)methoxy)-3-(3-(p-tolyl)ureido)phenyl)butanoic acid

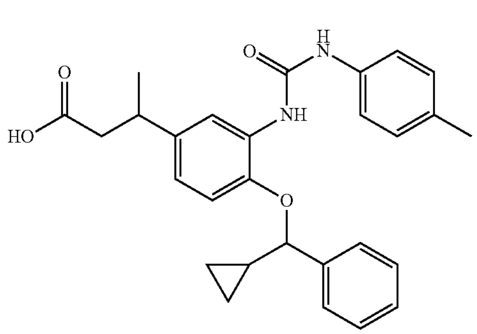 [SMILES: Cc1ccc(NC(=O)Nc2cc(C(C)CC(=O)O)ccc2OC(c2ccccc2)C2CC2)cc1]

Example 11 was obtained following the same procedure in Example 9 except that cyclopropyl(phenyl)methanol was used in the aryl ether formation. LC-MS Anal. Calc'd for $C_{28}H_{30}N_2O_4$ 458.22, found [M+H] 459.16. $T_r$=3.67 min (Method A). $^1$H NMR (500 MHz, DMSO-$d_6$) δ 9.44 (s, 1H), 8.12 (s, 1H), 8.03-7.94 (m, 1H), 7.48 (d, J=7.5 Hz, 2H), 7.39 (d, J=8.3 Hz, 2H), 7.33 (t, J=7.6 Hz, 2H), 7.27-7.20 (m, 1H), 7.11 (d, J=8.3 Hz, 2H), 6.80-6.69 (m, 1H), 6.61 (dt, J=8.3, 2.6 Hz, 1H), 4.72 (d, J=8.6 Hz, 1H), 2.98 (dq, J=14.5, 7.3 Hz, 1H), 2.41-2.28 (m, 2H), 2.26 (s, 3H), 1.47-1.36 (m, 1H), 1.11 (d, J=6.9 Hz, 3H), 0.71-0.61 (m, 1H), 0.57-0.41 (m, 3H)

Example 12

3-(4-(3-phenylpropoxy)-3-(3-(p-tolyl)ureido)phenyl)butanoic acid

Racemic

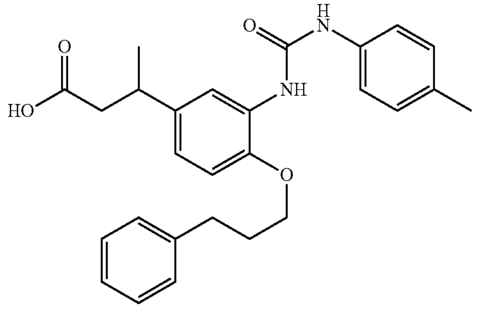 [SMILES: Cc1ccc(NC(=O)Nc2cc(C(C)CC(=O)O)ccc2OCCCc2ccccc2)cc1]

12A. (E)-1-(4-(cinnamyloxy)-3-nitrophenyl)ethanone

To a solution of 1-(4-hydroxy-3-nitrophenyl)ethanone (2 g, 11.04 mmol) in acetone (50 mL) was added potassium carbonate (3.05 g, 22.08 mmol). Then (E)-(3-bromoprop-1-en-1-yl)benzene (3.59 mL, 24.29 mmol) was added slowly. The solution turned from clear to orange/yellow suspension. After 16 h, LC-MS indicated small amount of product. Then it was heated at 60° C. for 1 h, started to see more product. It was cooled to RT. The reaction mixture was diluted with water (20 mL). The aqueous layer was further extracted with EtOAc (3×20 mL) and the combined organic extracts were washed with water, brine, dried over MgSO4, filtered and concentrated. Trituration with $CH_2Cl_2$ (10 mL) and Hexanes (50 mL) precipitated out a yellow solid. Filtration and drying under vacuum gave 12A (yellow solid, 2 g, 6.73 mmol, 60.9% yield). LC-MS Anal. Calc'd for $C_{17}H_{15}NO_4$ 297.10, did not show parent ion in MS, $T_r$=3.33 min (Method A). $^1$H NMR (400 MHz, CHLOROFORM-d) δ 8.45 (d, J=2.2 Hz, 1H), 8.16 (dd, J=8.8, 2.2 Hz, 1H), 7.46-7.40 (m, 2H), 7.38-7.32 (m, 2H), 7.32-7.28 (m, 1H), 7.22 (d, J=9.0 Hz, 1H), 6.82 (d, J=15.8 Hz, 1H), 6.39 (dt, J=15.9, 5.7 Hz, 1H), 4.95 (dd, J=5.6, 1.4 Hz, 2H), 2.61 (s, 3H)

3-(4-(3-phenylpropoxy)-3-(3-(p-tolyl)ureido)phenyl)butanoic acid (Racemic)

To a solution of NaH (0.148 g, 3.70 mmol) in THF (10 mL) at 0° C. was added ethyl 2-(diethoxyphosphoryl)acetate (0.673 mL, 3.36 mmol). After stirring for 1 h, a solution of 12A (0.5 g, 1.68 mmol) in THF was added. The resulting reaction mixture was then stirred at RT for 16 h. LC-MS indicated completion. It was quenched with 10 mL saturated aqueous $NH_4Cl$ and diluted with 20 mL EtOAc. The aqueous layer was further extracted with EtOAc (2×20 mL) and the combined organic extracts were washed with water, brine, dried over $MgSO_4$, filtered and concentrated. Purification via flash chromatography gave ethyl 3-(4-(cinnamyloxy)-3-nitrophenyl)but-2-enoate (yellow oil, 0.35 g, 0.953 mmol, 56.6% yield) as a mixture of E and Z isomers. To a stirred solution of a E and Z mixture of ethyl 3-(4-(cinnamyloxy)-3-nitrophenyl)but-2-enoate obtained above (150 mg, 0.408 mmol) in ethyl acetate (10 mL) was added palladium on carbon (43.4 mg, 0.041 mmol) and the suspension was hydrogenated (1 atm, balloon) for 1 h. LC-MS indicated completion. The suspension was filtered through a pad of Celite and the filter cake was rinsed with EtOAc (3×10 mL). Combined filtrate and rinses were concentrated in vacuo. Crude was used without purification in the subsequent step. To a solution of crude ethyl 3-(3-amino-4-(3-phenylpropoxy)phenyl)butanoate (100 mg, 0.293 mmol) obtained above in THF (4 mL) was added 1-isocyanato-4-methylbenzene (58.5 mg, 0.439 mmol). The resulting solution was stirred at RT for 12 h. The reaction mixture was concentrated and the crude ester was dissolved in THF (4.00 mL) and water (2.000 mL) then 1N aqueous sodium hydroxide (0.879 mL, 0.879 mmol) was added. MeOH (1 mL) was added to dissolve the precipitate and it turned into a clear yellow solution. After 3 days, reaction was complete by LC-MS. Most MeOH and THF was removed in vacuo and the crude was diluted with 2 mL of water, the pH was adjusted to ca. 4 using 1N aqueous HCl. The aqueous phase was then extracted with EtOAc (3×10 mL) and the combined organic extracts were washed with brine, dried over $Na_2SO_4$ and concentrated. Preparative HPLC gave 12B (light yellow oil, 9.1 mg, 0.020 mmol, 6.7% yield). LC-MS Anal. Calc'd for $C_{27}H_{30}N_2O_4$ 446.22, found [M+H] 447.17. $T_r$=3.78 min (Method A). $^1$H NMR (500 MHz, DMSO-$d_6$) δ 9.29 (s, 1H), 8.03 (d, J=2.0 Hz, 1H), 7.97 (s, 1H), 7.35 (d, J=8.4 Hz, 2H), 7.32-7.21 (m, 2H), 7.21-7.14 (m, 1H), 7.08 (d, J=8.4 Hz, 2H), 6.86 (d, J=8.4 Hz, 1H), 6.77 (dd, J=8.2, 2.2 Hz, 1H), 4.02 (t, J=6.4 Hz, 2H), 3.10-2.99 (m, 1H), 2.83-2.75 (m, 2H), 2.43 (dd, J=7.4, 4.0 Hz, 2H), 2.23 (s, 3H), 2.13-2.02 (m, 2H), 1.17 (d, J=6.9 Hz, 3H)

Example 13

Racemic 3-(4-(diisobutylamino)-3-(3-(3-methylisoxazol-5-yl)ureido)phenyl)butanoic acid

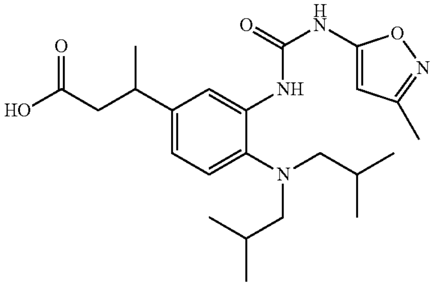 [SMILES: Cc1cc(NC(=O)Nc2cc(C(C)CC(=O)O)ccc2N(CC(C)C)CC(C)C)on1]

Example 13 was obtained following the procedure in Example 3 using 3C and 3-methylisoxazol-5-amine in the urea formation. LC-MS Anal. Calc'd for $C_{23}H_{34}N_4O_4$ 430.26, found [M+H] 431.4. $T_r$=0.93 min (Method B). $^1$H NMR (500 MHz, METHANOL-$d_4$) δ 7.92 (d, J=2.0 Hz, 1H), 7.11 (s, 1H), 7.00-6.87 (m, 1H), 6.06 (s, 1H), 3.30-3.13 (m, 1H), 2.64 (d, J=7.4 Hz, 5H), 2.55-2.45 (m, 1H), 2.25 (s, 3H), 1.77-1.62 (m, 2H), 1.31 (d, J=6.9 Hz, 3H), 0.88 (d, J=6.9 Hz, 12H)

Example 14

Racemate, Enantiomer 1 and Enantiomer 2

3-(4-(diisobutylamino)-3-(3-(p-tolyl)ureido)phenyl)-4,4,4-trifluorobutanoic acid

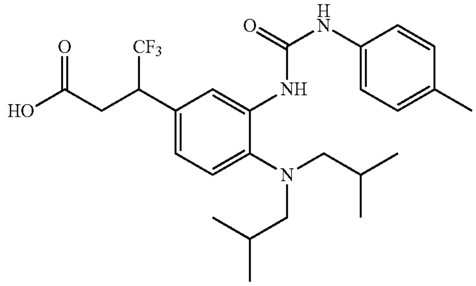

14A. 1-(4-(diisobutylamino)-3-nitrophenyl)-2,2,2-trifluoroethanol

TBAF (21.56 mL, 21.56 mmol) was added to a solution of 4-(diisobutylamino)-3-nitrobenzaldehyde (1 g, 3.59 mmol) and trimethyl(trifluoromethyl)silane (0.766 g, 5.39 mmol) in THF (10 mL) at 0° C. The resulting mixture was warmed up to RT and stirred for 12 h. LC-MS indicated completion. The reaction mixture was then treated with 5 mL of 1 N aqueous HCl. After stirring for 15 min, the product was extracted with EtOAc (2×30 mL). The combined organic extracts were washed with water, brine, dried over $Na_2SO_4$, filtered and concentrated. Purification via flash chromatography gave 14A (orange oil, 1.2 g, 3.44 mmol, 96% yield). LC-MS Anal. Calc'd for $C_{16}H_{23}F_3N_2O_3$ 348.17, found [M+H] 349.14. $T_r$=3.76 min (Method A). $^1$H NMR (400 MHz, CHLOROFORM-d) δ 7.84 (d, J=2.2 Hz, 1H), 7.47 (dd, J=8.8, 2.2 Hz, 1H), 7.13 (d, J=8.8 Hz, 1H), 4.97 (q, J=6.6 Hz, 1H), 2.96 (d, J=7.3 Hz, 4H), 1.93 (dquin, J=13.5, 6.8 Hz, 2H), 0.84 (d, J=6.6 Hz, 12H)

14B. 1-(4-(diisobutylamino)-3-nitrophenyl)-2,2,2-trifluoroethanone

To a solution of 14A (1.3 g, 3.73 mmol) in $CH_2Cl_2$ (50 mL) at 0° C. was added sodium bicarbonate (0.940 g, 11.20 mmol) followed by Dess-Martin Periodinane (2.374 g, 5.60 mmol). After stirring for 16 h, LC-MS indicated completion, the reaction mixture was then diluted with 20 mL of saturated aqueous $NaHCO_3$. After stirring for 15 min, the organic layer was separated and extracted with $CH_2Cl_2$ (2×20 mL). The combined organic extracts were washed with water, brine, dried over $Na_2SO_4$, filtered and concentrated. Purification via flash chromatography gave 14B (green oil, 0.9 g, 2.60 mmol, 69.6% yield). LC-MS Anal. Calc'd for $C_{16}H_{21}F_3N_2O_3$ 346.15, did not show parent ion in MS, $T_r$=3.88 min (Method A). $^1$H NMR (400 MHz, CHLOROFORM-d) δ 8.50-8.42 (m, 1H), 8.05-7.97 (m, 1H), 7.14 (d, J=9.2 Hz, 1H), 3.09 (d, J=7.5 Hz, 4H), 2.01 (dquin, J=13.5, 6.8 Hz, 2H), 0.88 (d, J=6.6 Hz, 12H)

14C. ethyl 3-(3-amino-4-(diisobutylamino)phenyl)-4,4,4-trifluorobutanoate

To a solution of NaH (0.254 g, 6.35 mmol) in THF (16 mL) at 0° C. was added ethyl 2-(diethoxyphosphoryl)acetate (1.156 mL, 5.77 mmol). After 30 min, it became a clear solution. Then 14B (1 g, 2.89 mmol) in THF (8.00 mL) was added. After stirring at RT for 1 h, LC-MS indicated completion. It was then quenched with 10 mL of saturated aqueous $NH_4Cl$. The aqueous layer was further extracted with EtOAc (3×20 mL) and the combined organic extracts were washed with water, brine, dried over $MgSO_4$, filtered and concentrated. Purification via flash chromatography gave ethyl 3-(4-(diisobutylamino)-3-nitrophenyl)-4,4,4-trifluorobut-2-enoate (E/Z geometry not defined) (yellow oil, 1 g, 2.401 mmol, 83% yield). To a stirred solution of above obtained ethyl 3-(4-(diisobutylamino)-3-nitrophenyl)-4,4,4-trifluorobut-2-enoate (550 mg, 1.321 mmol) in ethyl acetate (12 mL) was added palladium on carbon (141 mg, 0.132 mmol) and the suspension was hydrogenated (1 atm, balloon) for 2 h. LC-MS indicated completion. The suspension was filtered through a pad of Celite and the filter cake was rinsed with EtOAc (3×20 mL). Combined filtrate and rinses were concentrated in vacuo. Purification via flash chromatography gave 14C (light yellow oil, 200 mg, 0.515 mmol, 39.0% yield). LC-MS Anal. Calc'd for $C_{20}H_{31}F_3N_2O_2$ 388.23, found [M+H] 389.22. $T_r$=3.52 min (Method A). $^1$H NMR (400 MHz, CHLOROFORM-d) δ 7.01 (d, J=7.9 Hz, 1H), 6.73-6.54 (m, 2H), 4.18-4.11 (m, 2H), 4.08 (qd, J=7.1, 3.3 Hz, 2H), 3.83-3.72 (m, 1H), 2.99-2.91 (m, 1H), 2.85-2.76 (m, 1H), 2.59 (d, J=7.3 Hz, 4H), 1.74 (dquin, J=13.5, 6.8 Hz, 2H), 1.14 (t, J=7.2 Hz, 3H), 0.90 (d, J=6.6 Hz, 12H)

14D. Racemic 3-(4-(diisobutylamino)-3-(3-(p-tolyl)ureido)phenyl)-4,4,4-trifluorobutanoic acid To a solution of 14C (25 mg, 0.064 mmol) in THF (2 mL) was added 1-isocyanato-4-methylbenzene (12.85 mg, 0.097 mmol). The resulting solution was stirred at RT for 6 h. The reaction mixture was concentrated and the crude ester was dissolved in THF (2.000 mL) and water (1.000 mL) then 1N aqueous sodium hydroxide (0.193 mL, 0.193 mmol) was added. MeOH (1 mL) was added to dissolve the precipitate and it turned into a clear yellow solution. After 16 h, reaction was complete by LC-MS. Most MeOH and THF was removed in vacuo and the crude was diluted with 5 mL of water, the pH was adjusted to ca. 4 using 1N aqueous HCl. The aqueous phase was then extracted with EtOAc (3×10 mL) and the combined organic extracts were washed with brine, dried over $Na_2SO_4$ and concentrated. Preparative HPLC gave 14D (light yellow oil, 25.8 mg, 0.052 mmol, 81% yield). LC-MS Anal. Calc'd for $C_{26}H_{34}F_3N_3O_3$ 493.26, found [M+H] 494.20. $T_r$=3.83 min (Method A). $^1H$ NMR (500 MHz, DMSO-$d_6$) δ 9.39 (s, 1H), 8.01 (d, J=1.5 Hz, 1H), 7.85 (s, 1H), 7.36 (d, J=8.4 Hz, 2H), 7.20 (d, J=7.9 Hz, 1H), 7.09 (d, J=8.4 Hz, 2H), 6.97 (dd, J=8.2, 1.7 Hz, 1H), 3.89 (td, J=9.0, 5.7 Hz, 1H), 2.66 (d, J=6.9 Hz, 4H), 2.24 (s, 3H), 1.64 (dquin, J=13.4, 6.7 Hz, 2H), 0.84 (d, J=6.9 Hz, 12H)

Enantiomer 1 and Enantiomer 2 of 3-(4-(diisobutylamino)-3-(3-(p-tolyl)ureido)phenyl)-4,4,4-trifluorobutanoic acid The individual enantiomers were obtained by chiral separation of 14D (Method G); Enantiomer 1 $T_r$=9.50 min and enantiomer 2 $T_r$=11.50 min (Method H).

Enantiomer 1 (faster eluting): LC-MS Anal. Calc'd for $C_{26}H_{34}F_3N_3O_3$ 493.26, found [M+H] 494.5. $T_r$=1.07 min (Method A). $^1H$ NMR (400 MHz, CHLOROFORM-d) δ 8.28 (d, J=1.8 Hz, 1H), 8.14 (s, 1H), 7.71 (br. s., 1H), 7.19-7.06 (m, 5H), 7.00 (d, J=8.1 Hz, 1H), 4.06-3.91 (m, 1H), 3.07 (dd, J=16.6, 3.6 Hz, 1H), 2.82 (dd, J=16.5, 10.1 Hz, 1H), 2.55-2.38 (m, 4H), 2.33 (s, 3H), 1.56 (dquin, J=13.5, 6.7 Hz, 2H), 0.69 (dd, J=15.4, 6.6 Hz, 12H); Enantiomer 2 (slower eluting): LC-MS Anal. Calc'd for $C_{26}H_{34}F_3N_3O_3$ 493.26, found [M+H] 494.5. $T_r$=1.07 min (Method A). $^1H$ NMR (400 MHz, CHLOROFORM-d) δ 8.26 (d, J=2.0 Hz, 1H), 8.12 (s, 1H), 7.58 (br. s., 1H), 7.19-7.06 (m, 5H), 7.03-6.96 (m, 1H), 3.98 (quind, J=9.7, 3.9 Hz, 1H), 3.05 (dd, J=16.5, 3.7 Hz, 1H), 2.82 (dd, J=16.5, 10.3 Hz, 1H), 2.56-2.38 (m, 4H), 2.33 (s, 3H), 1.56 (dquin, J=13.5, 6.7 Hz, 2H), 0.70 (dd, J=14.7, 6.6 Hz, 12H)

Example 15

Racemic

3-(4-(diisobutylamino)-3-(3-(2-fluorophenyl)ureido)phenyl)-4,4,4-trifluorobutanoic acid

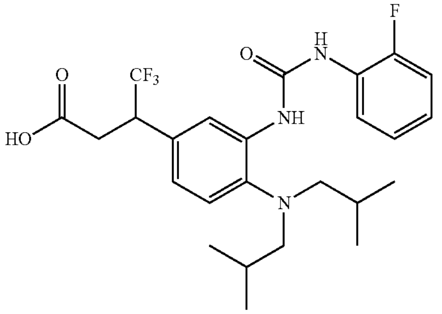 [SMILES: CC(C)CN(CC(C)C)c1ccc(C(CC(=O)O)C(F)(F)F)cc1NC(=O)Nc1ccccc1F]

Example 15 was obtained following the procedure of example 14 using the corresponding isocyanate. LC-MS Anal. Calc'd for $C_{25}H_{31}F_4N_3O_3$ 497.23, found [M+H] 498.19. $T_r$=3.75 min (Method A). $^1H$ NMR (500 MHz, DMSO-$d_6$) δ 9.37 (s, 1H), 8.11 (s, 1H), 8.00 (td, J=8.3, 1.7 Hz, 1H), 7.91 (d, J=2.0 Hz, 1H), 7.31-7.10 (m, 3H), 7.08-6.93 (m, 2H), 3.93-3.85 (m, 1H), 2.99-2.90 (m, 1H), 2.80 (dd, J=16.3, 8.9 Hz, 1H), 2.69 (d, J=6.9 Hz, 4H), 1.66 (dquin, J=13.2, 6.6 Hz, 2H), 0.83 (d, J=6.4 Hz, 12H)

Examples 16-31

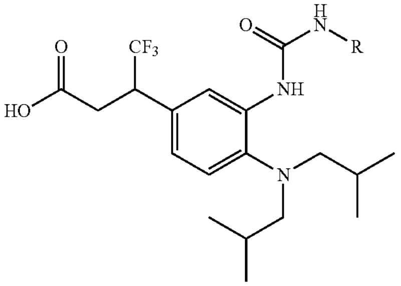

These compounds were obtained following the procedures in Example 14 using the corresponding isocyanate.

| Ex. No. | Name | R | Tr (min) | [M + H]$^+$ |
|---|---|---|---|---|
| 16 | 3-(4-(diisobutylamino)-3-(3-(4-phenoxyphenyl)ureido)phenyl)-4,4,4-trifluorobutanoic acid | 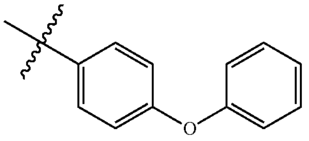 [SMILES: *c1ccc(Oc2ccccc2)cc1] | 2.35$^F$ | 572.12 |
| 17 | 3-(3-(3-(4-chlorophenyl)ureido)-4-(diisobutylamino)phenyl)-4,4,4-trifluorobutanoic acid | 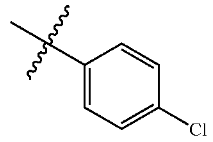 [SMILES: *c1ccc(Cl)cc1] | 2.24$^F$ | 514.09 |
| 18 | 3-(4-(diisobutylamino)-3-(3-(4-fluorophenyl)ureido)phenyl)-4,4,4-trifluorobutanoic acid | 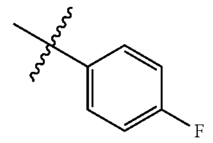 [SMILES: *c1ccc(F)cc1] | 2.11$^F$ | 498.14 |

-continued

| Ex. No. | Name | R | Tr (min) | [M + H]+ |
|---|---|---|---|---|
| 19 | 3-(3-(3-(2,4-dichlorophenyl)ureido)-4-(diisobutylamino)phenyl)-4,4,4-trifluorobutanoic acid | 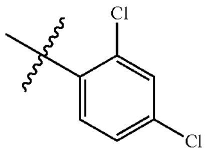 [SMILES: *c1ccc(Cl)cc1Cl] | 2.44F | 548.04 |
| 20 | 3-(4-(diisobutylamino)-3-(3-phenylureido)phenyl)-4,4,4-trifluorobutanoic acid | 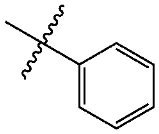 [SMILES: *c1ccccc1] | 2.08F | 480.17 |
| 21 | 3-(4-(diisobutylamino)-3-(3-(4-isopropylphenyl)ureido)phenyl)-4,4,4-trifluorobutanoic acid | 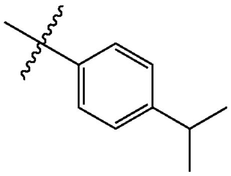 [SMILES: *c1ccc(C(C)C)cc1] | 2.36F | 522.17 |
| 22 | 3-(4-(diisobutylamino)-3-(3-(4-ethylphenyl)ureido)phenyl)-4,4,4-trifluorobutanoic acid | 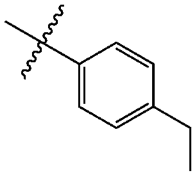 [SMILES: *c1ccc(CC)cc1] | 2.27F | 508.18 |
| 23 | 3-(4-(diisobutylamino)-3-(3-(4-(trifluoromethyl)phenyl)ureido)phenyl)-4,4,4-trifluorobutanoic acid | 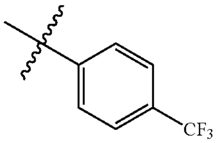 [SMILES: *c1ccc(C(F)(F)F)cc1] | 2.32F | 548.09 |
| 24 | 3-(4-(diisobutylamino)-3-(3-(4-methoxyphenyl)ureido)phenyl)-4,4,4-trifluorobutanoic acid | 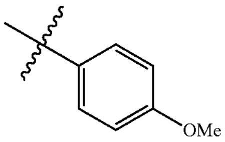 [SMILES: *c1ccc(OC)cc1] | 2.04F | 510.14 |
| 25 | 3-(4-(diisobutylamino)-3-(3-(o-tolyl)ureido)phenyl)-4,4,4-trifluorobutanoic acid | 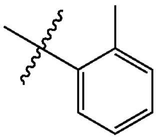 [SMILES: *c1ccccc1C] | 1.87F | 494.17 |
| 26 | 3-(3-(3-(2-chloro-4-methylphenyl)ureido)-4-(diisobutylamino)phenyl)-4,4,4-trifluorobutanoic acid | 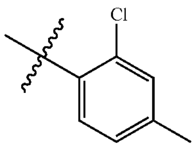 [SMILES: *c1ccc(C)cc1Cl] | 2.34F | 528.15 |
| 27 | 3-(3-(3-(4-benzyphenyl)ureido)-4-(diisobutylamino)phenyl)-4,4,4-trifluorobutanoic acid | 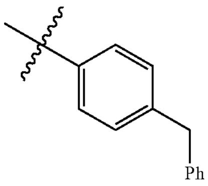 [SMILES: *c1ccc(Cc2ccccc2)cc1] | 2.39F | 570.17 |

-continued

| Ex. No. | Name | R | Tr (min) | [M + H]+ |
|---|---|---|---|---|
| 28 | 3-(3-(3-(4-(difluoromethoxy)phenyl)ureido)-4-(diisobutylamino)phenyl)-4,4,4-trifluorobutanoic acid | 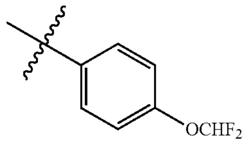 [SMILES: *c1ccc(OC(F)F)cc1] | 2.16F | 546.13 |
| 29 | 3-(4-(diisobutylamino)-3-(3-(4-ethoxyphenyl)ureido)phenyl)-4,4,4-trifluorobutanoic acid | 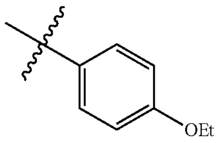 [SMILES: *c1ccc(OCC)cc1] | 1.87F | 524.19 |
| 30 | 3-(3-(3-(2,4-difluorophenyl)ureido)-4-(diisobutylamino)phenyl)-4,4,4-trifluorobutanoic acid | 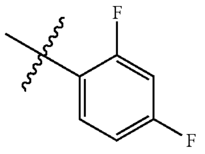 [SMILES: *c1ccc(F)cc1F] | 2.17F | 516.12 |
| 31 | 3-(4-(diisobutylamino)-3-(3-(m-tolyl)ureido)phenyl)-4,4,4-trifluorobutanoic acid | 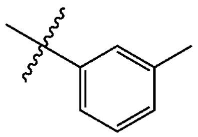 [SMILES: *c1cccc(C)c1] | 2.17F | 494.18 |

Example 32

1-(5-(2-(1H-tetrazol-5-yl)ethyl)-2-(diisobutylamino)phenyl)-3-(p-tolyl)urea

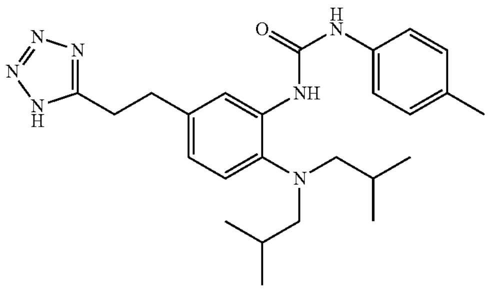 [SMILES: Cc1ccc(NC(=O)Nc2cc(CCc3nnn[nH]3)ccc2N(CC(C)C)CC(C)C)cc1]

32A: (E)-4-(2-(1H-tetrazol-5-yl)vinyl)-N,N-diisobutyl-2-nitroaniline

An oven dried, two necked round bottom flask containing a stirring bar was charged with 4-bromo-N,N-diisobutyl-2-nitroaniline (1 g, 3.04 mmol), 5-vinyl-1H-tetrazole (0.292 g, 3.04 mmol), palladium(II) acetate (6.82 mg, 0.030 mmol) and triethanolamine (7 mL). The mixture was heated and stirred at 100° C. for 10 h. LC-MS indicated only small amount of desired product with lots of starting material remaining. Added another 0.01 eq of palladium(II) acetate. The mixture was heated and stirred at 100° C. for another 48 h. LC-MS indicated completion. After cooling to RT, it was diluted with DCM (20 ml), passed through a plug of silica gel, washed with 15% (v/v) MeOH in DCM, the organic rinses were concentrated and purification via flash chromatography gave 32A (orange solid, 0.699 g, 2.030 mmol, 66.8% yield). LC-MS Anal. Calc'd for $C_{17}H_{24}N_6O_2$ 344.20, found [M+H] 345.3. $T_r$=1.08 min (Method B).

32B: 4-(2-(1H-tetrazol-5-yl)ethyl)-N1,N1-diisobutylbenzene-1,2-diamine

To a solution of 32A (50 mg, 0.145 mmol) in MeOH (10 mL) under a $N_2$ atmosphere was added 10% Pd/C (0.154 mg, 1.452 μmol). The mixture was degassed by house vacuum, and then stirred under hydrogen atmosphere (Hydrogen balloon) for 14 h. The reaction mixture was filtered and concentrated to give 32B as light yellow oil which used in next step without purification. LC-MS Anal. Calc'd for $C_{17}H_{28}N_6$ 316.44, found [M+H] 317.2. $T_r$=0.71 min (Method A).

1-(5-(2-(1H-tetrazol-5-yl)ethyl)-2-(diisobutylamino)phenyl)-3-(p-tolyl)urea

To a solution of 32C (30 mg, 0.095 mmol) in THF (1 mL) was added 1-isocyanato-4-methylbenzene (0.024 mL, 0.190 mmol). The reaction was stirred 2 h at RT, then quenched with 0.03 mL of N,N-dimethylethylenediamine. The crude material was purified by preparative HPLC to afford the title compound (2.9 mg, 6.45 μmol, 7% yield). LC-MS Anal. Calc'd for $C_{25}H_{35}N_7O$ 449.29. found [M+H] 450.3. $T_r$=3.44 min (Method A). $^1$H NMR (500 MHz, METHANOL-$d_4$) δ 7.84 (d, J=1.5 Hz, 1H), 7.37-7.22 (m, 3H), 7.19-7.06 (m, 3H), 3.25 (s, 2H), 3.05 (s, 2H), 2.60 (d, J=7.4 Hz, 4H), 2.31-2.22 (m, 3H), 1.78-1.59 (m, 2H), 0.84 (d, J=6.9 Hz, 12H).

Example 33

1-(5-(2-(1H-tetrazol-5-yl)ethyl)-2-(diisobutylamino) phenyl)-3-(4-fluorophenyl)urea

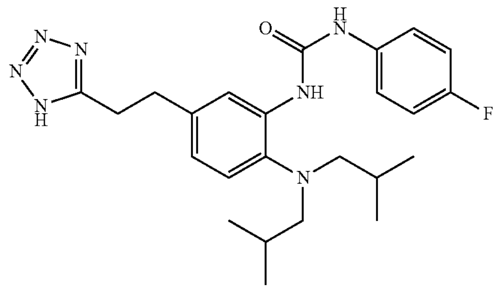 [SMILES: CC(C)CN(CC(C)C)c1ccc(CCc2nnn[nH]2)cc1NC(=O)Nc1ccc(F)cc1]

33 was obtained following the procedures in example 32 except that 4-fluoroaniline was used in the urea formation. LC-MS Anal. Calc'd for $C_{24}H_{32}FN_7O$ 453.27. found [M+H] 454.27. $T_r$=2.21 min (Method A). $^1H$ NMR (500 MHz, METHANOL-$d_4$) δ 7.61 (s, 1H), 7.48-7.33 (m, 3H), 7.00 (dt, J=15.0, 8.9 Hz, 3H), 3.33-3.20 (m, 2H), 3.17-3.04 (m, 2H), 2.78-2.47 (m, 4H), 1.82-1.54 (m, 2H), 0.88 (br. s., 12H)

Example 34

2-(1-(4-(diisobutylamino)-3-(3-(p-tolyl)ureido-phenyl)cyclopropyl)acetic acid

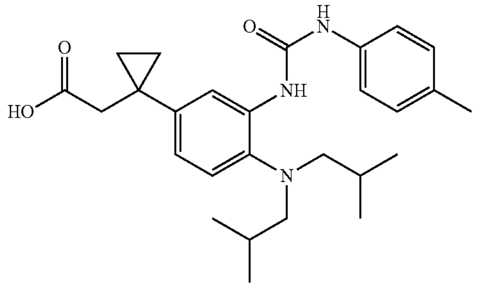 [SMILES: Cc1ccc(NC(=O)Nc2cc(C3(CC(=O)O)CC3)ccc2N(CC(C)C)CC(C)C)cc1]

34A: 2-(4-fluoro-3-nitrophenyl)acetonitrile

To a solution of 4-(bromomethyl)-1-fluoro-2-nitrobenzene (1 g, 4.27 mmol) in acetonitrile (5 mL) was added tetraethylammonium cyanide (0.801 g, 5.13 mmol). The resulting deep green solution was stirred at RT for 4 h. The solvent was then removed in vacuo, purification via flash chromatography gave 34A (light yellow oil, 617 mg, 3.43 mmol, 80% yield). LC-MS Anal. Calc'd for $C_8H_5FN_2O_2$ 180.03, did not show paretn ion, $T_r$=0.74 min (Method B).

34B: 2-(4-(diisobutylamino)-3-nitrophenyl)acetonitrile 34A (600 mg, 3.33 mmol) and diisobutylamine (2152 mg, 16.65 mmol) were heated at 130° C. for 2 h. After cooling to RT purification via flash chromatography gave 34B (orange oil, 579 mg, 2.001 mmol, 60.1% yield). LC-MS Anal. Calc'd for $C_{16}H_{23}N_3O_2$ 289.18, found [M+H] 290.9. $T_r$=1.12 min (Method B).

34C: 1-(4-(diisobutylamino)-3-nitrophenyl)cyclopropanecarbonitrile

To a solution of 34B (400 mg, 1.382 mmol) and 1-bromo-2-chloroethane (0.172 mL, 2.073 mmol) in DMF (10 mL) at 0° C. under argon was added NaH (138 mg, 3.46 mmol). The solution darkened. After 10 min, ice bath was removed and the mixture was warmed up to RT. After 30 min at RT, LC-MS indicated complete conversion to the desired product. The reaction mixture was quenched with saturated aqueous ammonium chloride and then diluted with water and EtOAc. The layers were separated and the aqueous phase was extracted with EtOAc (2×20 mL). The organic extracts were combined, washed with water and brine, dried over $Na_2SO_4$, filtered and concentrated. Purification via flash chromatography gave 34C (orange oil, 331 mg, 1.049 mmol, 76% yield). LC-MS Anal. Calc'd for $C_{18}H_{25}N_3O_2$ 315.19, found [M+H] 316.4. $T_r$=1.18 min (Method B).

34D: 1-(4-(diisobutylamino)-3-nitrophenyl)cyclopropanecarboxylic acid

To a solution of 34C (280 mg, 0.888 mmol) in EtOH (5 mL) was added a solution of NaOH (533 mg, 13.32 mmol) in Water (5 mL), and the mixture was heated to 100° C. for 16 h. LC-MS indicated 60% desired acid and 40% primary amide. The reaction mixture was heated at 100° C. for another 8 h. LC-MS indicated no improvement. It was then cooled to RT. concentrated in vacuo, diluted with 5 ml of water, acidified with 1N aqueous HCl to pH=ca. 2. Then extracted with EtOAc (2×20 ml). The combined organic extracts were washed with water and brine, dried over $Na_2SO_4$, filtered and concentrated. Purification via preparative HPLC gave 34D (123 mg, 0.368 mmol, 41.4% yield) LC-MS Anal. Calc'd for $C_{18}H_{26}N_2O_4$ 334.19, found [M+H] 334.8. $T_r$=1.09 min (Method B). $^1H$ NMR (400 MHz, CHLOROFORM-d) δ 9.45-9.17 (m, 1H), 7.72 (d, J=2.2 Hz, 1H), 7.41 (dd, J=8.7, 2.3 Hz, 1H), 7.12 (d, J=8.8 Hz, 1H), 3.05-2.88 (m, 4H), 1.93 (dt, J=13.5, 6.8 Hz, 2H), 1.79-1.63 (m, 2H), 1.36-1.23 (m, 2H), 0.95-0.79 (m, 12H)

34E: 2-(1-(4-(diisobutylamino)-3-nitrophenyl)cyclopropyl)acetic acid

A solution of 34D (159 mg, 0.475 mmol) in DCM (5 mL) was added oxalyl chloride (0.083 mL, 0.951 mmol) and DMF (0.368 μl, 4.75 μmol), the reaction mixture was stirred at RT for 2 h. It was then concentrated in vacuo, dried under high vacuum for 1 h. The crude material was dissolved in THF (3 mL) and acetonitrile (3 mL), cooled to 0° C. and trimethylsilyldiazomethane (2.377 mL, 4.75 mmol) was added. The reaction mixture was gradually warm up to RT over 4.5 h. The it was diluted with EtOAc, washed with water and brine, the solvent was evaporated. To the residue was added silver oxide (551 mg, 2.377 mmol), DMF (4 mL) and water (2 mL). It was stirred at 120° C. for 15 min, then cooled to RT, filtered through a pad of Celite, rinsed with EtOAc. After concentration, purification via preparative HPLC gave 34E (yellow oil, 29.7 mg, 0.085 mmol, 17.9% yield) LC-MS Anal. Calc'd for $C_{19}H_{28}N_2O_4$ 348.20, found [M+H] 349.3. $T_r$=1.12 min (Method B).

34F: 2-(1-(3-amino-4-(diisobutylamino)phenyl)cyclopropyl)acetic acid

A solution of 34E (29 mg, 0.083 mmol) in MeOH (5 mL) under a $N_2$ atmosphere was added 10% Pd—C (8.86 mg, 8.32 μmol). The mixture was degassed by house vacuum, and then stirred under a hydrogen atmosphere (Hydrogen balloon) for 2 h. The reaction mixture was filtered through a Celite pad and concentrated to obtain 34F (13.1 mg, 0.041 mmol, 49.4% yield) as a light yellow oil. LC-MS Anal. Calc'd for $C_{19}H_{28}N_2O_4$ 318.23, found [M+H] 319.3. $T_r$=0.79 min (Method B).

2-(1-(4-(diisobutylamino)-3-(3-(p-tolyl)ureido)phenyl)cyclopropyl)acetic acid

To a solution of 34F (13 mg, 0.041 mmol) in THF (1 mL) was added 1-isocyanato-4-methylbenzene (10.87 mg, 0.082 mmol). The solution was stirred 3 h at RT, then concentrated under vacuo and purified by HPLC to obtain the 34G (1.2 mg, 2.66 μmol, 6.51% yield). LC-MS Anal. Calc'd for $C_{27}H_{37}N_3O_3$ 451.28, found [M+H] 452.5. $T_r$=0.95 min (Method B). $^1H$ NMR (500 MHz, METHANOL-$d_4$) δ 7.89 (d, J=2.0 Hz, 1H), 7.28 (d, J=7.9 Hz, 2H), 7.11 (d, J=8.4 Hz, 2H), 7.06-6.97 (m, 2H), 2.60-2.52 (m, 4H), 2.35-2.24 (m, 3H), 1.97 (s, 2H), 1.66 (s, 2H), 1.00-0.91 (m, 4H), 0.83 (d, J=6.4 Hz, 12H).

Example 35

(R)-3-(4-(diisobutylamino)-3-(3-(quinoxalin-6-yl)ureido)phenyl)butanoic acid

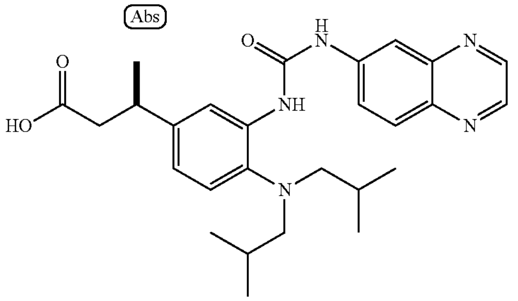 [SMILES: CC(C)CN(CC(C)C)c1ccc([C@H](C)CC(=O)O)cc1NC(=O)Nc1ccc2nccnc2c1]

35A. 4-bromo-N,N-diisobutyl-2-nitroaniline 4-bromo-1-fluoro-2-nitrobenzene (7 g, 31.8 mmol) and diisobutylamine (12.23 ml, 70.0 mmol) were heated at 130° C. for 3 h. It was then cooled to RT, purification by flash chromatography gave 35A (bright red solid, 8.19 g, 24.88 mmol, 78% yield). LC-MS Anal. Calc'd for $C_{14}H_{21}BrN_2O_2$ 328.08, found [M+3] 331.03, $T_r$=2.63 min (Method A).

35B. (E)-methyl 3-(4-(diisobutylamino)-3-nitrophenyl)but-2-enoate

To a solution of 35A (2 g, 6.07 mmol) in DMF (20 mL) was added (E)-methyl but-2-enoate (1.216 g, 12.15 mmol), tetrabutylammonium bromide (0.392 g, 1.215 mmol), triethylamine (1.693 mL, 12.15 mmol) and dichlorobis(tri-o-tolylphosphine)-palladium(II) (0.239 g, 0.304 mmol). The mixture was sparged with nitrogen for 10 min, then it was sealed and heated at 110° C. overnight. The reaction mixture was cooled to rt and filtered through packed Celite and diluted with water and EtOAc. The organic phase was separated and washed with brine, dried over anhydrous $MgSO_4$, filtered and concentrated to give the crude product. Purification via flash chromatography gave 35B (1.5 g, 4.31 mmol, 71% yield).

35C. (R)-methyl 3-(3-amino-4-(diisobutylamino)phenyl)butanoate

To 35B (1.5 g, 4.31 mmol) in MeOH (50 mL) at rt was added 10% Pd/C (0.644 g, 0.607 mmol). The mixture was evacuated and back-filled with $H_2$ (3×), and the mixture was stirred under $H_2$ atmosphere overnight. The reaction mixture was evacuated with vacuum and back-filled with nitrogen, then it was filtered through packed Celite and the filtrate was concentrated. Purification via flash chromatography gave racemic 35C (0.85 g, 2.60 mmol, 42.8% yield) as colorless liquid. Chiral separation of racemic 35C by Method G, gave the faster eluting enantiomer 1 (0.410 g, 1.267 mmol, 48%) $T_r$=1.80 min (Method I) and the slower eluting enantiomer 2 (0.40 g, 1.24 mmol, 46%) $T_r$=2.19 min (Method I), both as light brown oils absolute stereochemistry unknown.

35D. (R)-methyl 3-(4-(diisobutylamino)-3-(3-(quinoxalin-6-yl)ureido)phenyl)butanoate To a solution of 35C enantiomer 1 (0.0251 g, 0.078 mmol) in THF (1.205 ml) was added 4-nitrophenyl carbonochloridate (0.017 g, 0.082 mmol). The reaction was stirred at rt for 30 min. To this reaction were added quinoxalin-6-amine (0.034 g, 0.235 mmol) and triethylamine (0.033 ml, 0.235 mmol). The reaction was heated at 50° C. overnight, then allowed to cool to RT. The reaction was diluted with $H_2O$ and EtOAc. The layers were separated and the aqueous phase was extracted with EtOAc (3×). The organic phases were combined, dried over $Na_2SO_4$, filtered and concentrated to give 35D as a brown residue. The crude material was used without further purification.

(R)-3-(4-(diisobutylamino)-3-(3-(quinoxalin-6-yl)ureido)phenyl)butanoic acid

To a solution of 35D (0.039 g, 0.079 mmol) in tetrahydrofuran (0.088 ml) and MeOH (0.044 ml) was added a 1.5 M lithium hydroxide aqueous solution (0.529 ml, 0.793 mmol). The mixture was heated at 70° C. for 5 h, then allowed to stir at rt overnight. The reaction was neutralized with 1 N HCl (0.79 mL) and diluted with EtOAc. The layers were separated and the aqueous phase was extracted with EtOAc (3×). The organic phases were combined and the solvent was evaporated to give the crude product as a red residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (16.0 mg, 0.033 mmol, 41% yield). Anal. Calc'd for $C_{27}H_{35}N_5O_3$ 477.27, found [M+H] 478.4, $T_r$=1.43 min (Method C). $^1H$ NMR (500 MHz, METHANOL-$d_4$) δ 8.79 (d, J=2.0 Hz, 1H), 8.72 (d, J=2.0 Hz, 1H), 8.26 (d, J=2.0 Hz, 1H), 8.11-8.06 (m, 1H), 8.05-7.99 (m, 1H), 7.94 (d, J=2.5 Hz, 1H), 7.14 (d, J=7.9 Hz, 1H), 6.93 (dd, J=7.9, 2.0 Hz, 1H), 3.30-3.22 (m, 1H), 3.02 (s, 1H), 2.89 (s, 1H), 2.68 (d, J=6.9 Hz, 4H), 2.59-2.48 (m, 1H), 1.75 (dt, J=13.4, 6.7 Hz, 2H), 1.35 (d, J=6.9 Hz, 3H), 0.92 (d, J=6.9 Hz, 12H).

Example 36

(S)-3-(4-(diisobutylamino)-3-(3-(quinoxalin-6-yl) ureido)phenyl)butanoic acid

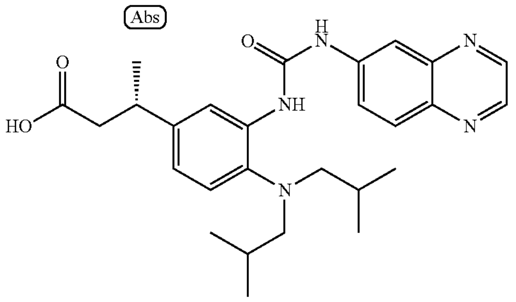 [SMILES: CC(C)CN(CC(C)C)c1ccc([C@@H](C)CC(=O)O)cc1NC(=O)Nc1ccc2nccnc2c1]

Example 36 was prepared following the procedure for Example 35 using 35C enantiomer 2 and quinoxalin-6-amine in the urea formation. Anal. Calc'd for $C_{27}H_{35}N_5O_3$ 477.27, found [M+H] 478.4, $T_r$=1.39 min (Method C); $^{1}$H NMR (500 MHz, METHANOL-$d_4$) δ 8.79 (d, J=1.5 Hz, 1H), 8.72 (d, J=2.0 Hz, 1H), 8.26 (d, J=2.5 Hz, 1H), 8.11-8.06 (m, 1H), 8.05-8.00 (m, 1H), 7.98 (br s, 1H), 7.94 (d, J=2.0 Hz, 1H), 7.14 (d, J=7.9 Hz, 1H), 6.93 (dd, J=7.9, 2.0 Hz, 1H), 3.31-3.22 (m, 1H), 3.02 (s, 1H), 2.90 (s, 1H), 2.68 (d, J=7.4 Hz, 4H), 2.65 (m, 1H), 2.54 (dd, J=15.1, 8.7 Hz, 1H), 1.75 (dquin, J=13.4, 6.7 Hz, 2H), 1.35 (d, J=6.9 Hz, 3H), 0.92 (d, J=6.4 Hz, 12H).

Example 37

(R)-3-(4-(diisobutylamino)-3-(3-(pyrimidin-5-yl) ureido)phenyl)butanoic acid

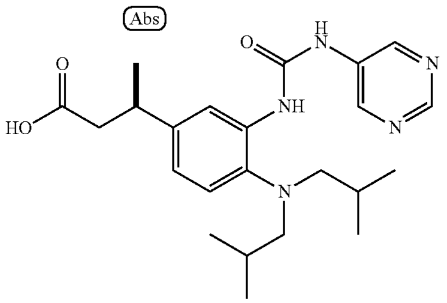 [SMILES: CC(C)CN(CC(C)C)c1ccc([C@H](C)CC(=O)O)cc1NC(=O)Nc1cncnc1]

Example 37 was prepared following the procedure for Example 35 utilizing 35C enantiomer 1 and pyrimidin-5-amine Anal. Calc'd for $C_{23}H_{33}N_5O_3$ 427.26, found [M+H] 428.3, $T_r$=1.96 min(Method D); $^{1}$H NMR (500 MHz, METHANOL-$d_4$) δ 9.00 (s, 2H), 8.80 (s, 1H), 7.93 (d, J=2.0 Hz, 1H), 7.14 (d, J=8.4 Hz, 1H), 6.93 (dd, J=8.4, 2.0 Hz, 1H), 3.31-3.20 (m, 1H), 3.02 (s, 1H), 2.90 (s, 1H), 2.66 (d, J=6.9 Hz, 4H), 2.64 (d, J=6.4 Hz, 1H), 2.53 (dd, J=15.1, 8.7 Hz, 1H), 1.73 (dquin, J=13.5, 6.7 Hz, 2H), 1.33 (d, J=6.9 Hz, 3H), 0.92 (d, J=6.9 Hz, 12H).

Example 38

(S)-3-(4-(diisobutylamino)-3-(3-(pyrimidin-5-yl) ureido)phenyl)butanoic acid

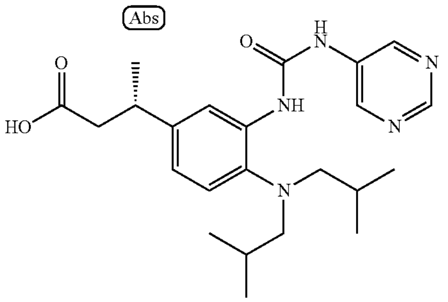 [SMILES: CC(C)CN(CC(C)C)c1ccc([C@@H](C)CC(=O)O)cc1NC(=O)Nc1cncnc1]

Example 38 was prepared following the procedure for Example 35 using the 35C enantiomer 2 and pyrimidin-5-amine in the urea formation. Anal. Calc'd for $C_{23}H_{33}N_5O_3$ 427.26, found [M+H] 428.3, $T_r$=1.93 min (Method D); $^{1}$H NMR (500 MHz, METHANOL-$d_4$) δ 9.00 (s, 2H), 8.79 (s, 1H), 7.93 (d, J=2.0 Hz, 1H), 7.14 (d, J=7.9 Hz, 1H), 6.94 (dd, J=8.2, 2.2 Hz, 1H), 3.30-3.19 (m, 1H), 3.02 (s, 1H), 2.90 (s, 1H), 2.67 (d, J=6.9 Hz, 4H), 2.63 (d, J=5.9 Hz, 1H), 2.53 (dd, J=15.1, 8.7 Hz, 1H), 1.73 (dquin, J=13.4, 6.7 Hz, 2H), 1.33 (d, J=6.9 Hz, 3H), 0.92 (d, J=6.9 Hz, 12H).

Example 39

(S)-3-(4-(diisobutylamino)-3-(3-(2-methylpyrimidin-5-yl)ureido)phenyl)butanoic acid

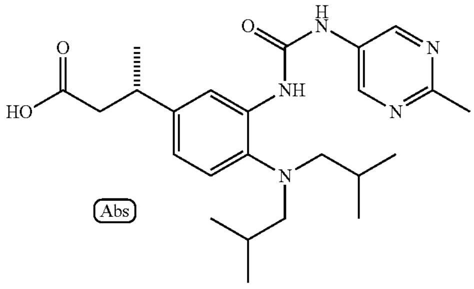 [SMILES: Cc1ncc(NC(=O)Nc2cc([C@@H](C)CC(=O)O)ccc2N(CC(C)C)CC(C)C)cn1]

Example 39 was prepared following the procedure for Example 35 using 35C enantiomer 2 and 2-methylpyrimidin-5-amine Anal. Calc'd for $C_{24}H_{35}N_5O_3$ 441.27, found [M+H] 442.3, $T_r$=1.22 min (Method C).

Example 40

(R)-3-(4-(diisobutylamino)-3-(3-(2-methylpyrimidin-5-yl)ureido)phenyl)butanoic acid

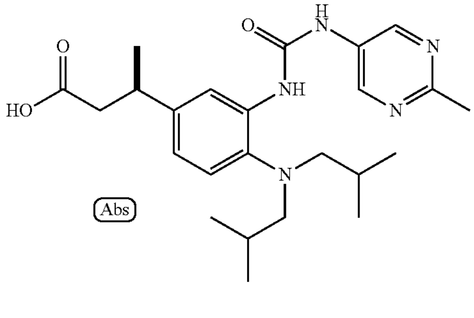 [SMILES: Cc1ncc(NC(=O)Nc2cc([C@H](C)CC(=O)O)ccc2N(CC(C)C)CC(C)C)cn1]

Example 40 was prepared following the procedure for Example 35 with 35C enantiomer 1 and 2-methyl pyrimidin-5-amine Anal. Calc'd for $C_{24}H_{35}N_5O_3$ 441.27, found [M+H] 442.2, $T_r$=1.27 min (Method C).

Example 41

(R)-3-(4-(diisobutylamino)-3-(3-(p-tolyl)ureido)phenyl)butanoic acid

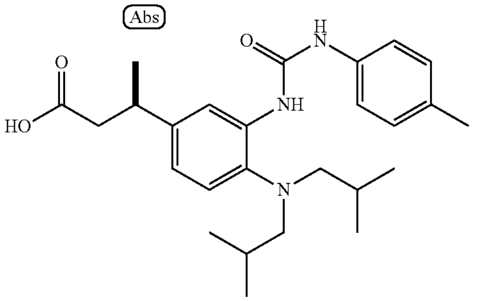 [SMILES: Cc1ccc(NC(=O)Nc2cc([C@H](C)CC(=O)O)ccc2N(CC(C)C)CC(C)C)cc1]

Example 41 was prepared following the procedure for Example 35 utilizing 35C enantiomer 1 and paratoluyliso-cyanate. Anal. Calc'd for $C_{23}H_{33}N_5O_3$ 439.2, found [M+H] 440.2, $T_r$=1.02 min (Method B). $^1H$ NMR (500 MHz, METHANOL-$d_4$) δ 7.85 (d, J=2.0 Hz, 1H), 7.26 (d, J=8.4 Hz, 2H), 7.11-7.00 (m, 3H), 6.84 (dd, J=8.4, 2.0 Hz, 1H), 4.29 (br. s., 3H), 2.63-2.54 (m, 5H), 2.51-2.40 (m, 1H), 2.28 (s, 3H), 1.70-1.53 (m, 2H), 1.28 (d, J=6.9 Hz, 3H), 0.82 (d, J=6.4 Hz, 12H)

Example 42

(R)-3-(4-(diisobutylamino)-3-(3-(5-methylisoxazol-3-yl)ureido)phenyl)butanoic acid

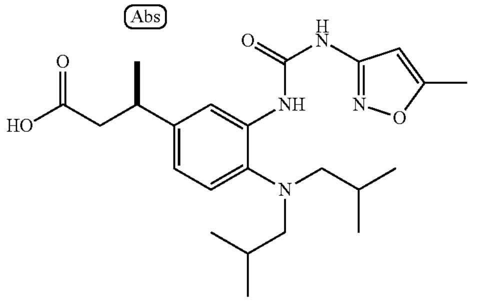 [SMILES: Cc1cc(NC(=O)Nc2cc([C@H](C)CC(=O)O)ccc2N(CC(C)C)CC(C)C)no1]

Example 42 was prepared following the procedure for Example 35 utilizing 35C enantiomer 1 and 5-methylisox-azol-3-amine Anal. Calc'd for $C_{23}H_{34}N_4O_4$ 430.26, found [M+H] 431.4, $T_r$=1.02 min (Method B). $^1H$ NMR (500 MHz, METHANOL-$d_4$) δ 7.88 (d, J=2.0 Hz, 1H), 7.09 (d, J=8.4 Hz, 1H), 6.89 (dd, J=7.9, 2.0 Hz, 1H), 6.30 (s, 1H), 3.25-3.13 (m, 1H), 2.65 (d, J=6.9 Hz, 4H), 2.60 (dd, J=15.1, 6.2 Hz, 1H), 2.47 (dd, J=15.1, 8.7 Hz, 1H), 2.37 (s, 3H), 1.68 (dt, J=13.4, 6.7 Hz, 2H), 1.29 (d, J=6.9 Hz, 3H), 0.85 (d, J=6.4 Hz, 12H).

Example 43

(S)-3-(4-(diisobutylamino)-3-(3-(p-tolyl)ureido)phenyl)butanoic acid

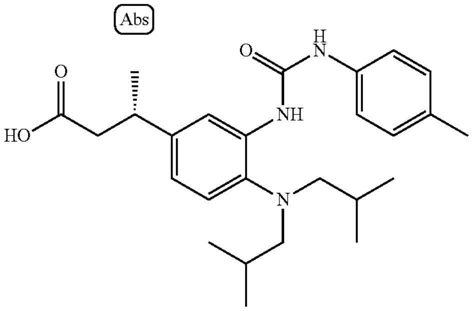 [SMILES: Cc1ccc(NC(=O)Nc2cc([C@@H](C)CC(=O)O)ccc2N(CC(C)C)CC(C)C)cc1]

Example 43 was prepared following the procedure for Example 35 using the 35C enantiomer 2 and paratoluyliso-cyanate. Anal. Calc'd for $C_{23}H_{33}N_5O_3$ 439.2, found [M+H] 440.2, $T_r$=1.02 min (Method B). $^1H$ NMR (500 MHz, METHANOL-$d_4$) δ 7.85 (d, J=2.0 Hz, 1H), 7.26 (d, J=8.4 Hz, 2H), 7.11-7.00 (m, 3H), 6.84 (dd, J=8.4, 2.0 Hz, 1H), 4.29 (br. s., 3H), 2.63-2.54 (m, 5H), 2.51-2.40 (m, 1H), 2.28 (s, 3H), 1.70-1.53 (m, 2H), 1.28 (d, J=6.9 Hz, 3H), 0.82 (d, J=6.4 Hz, 12H).

Example 44

(S)-3-(4-(diisobutylamino)-3-(3-(5-methylisoxazol-3-yl)ureido)phenyl)butanoic acid

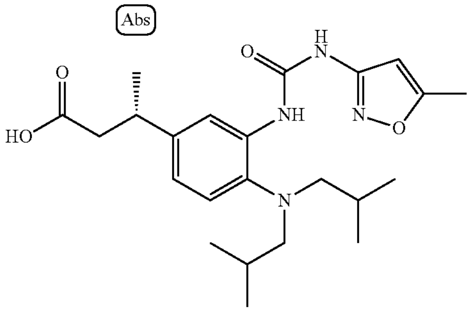 [SMILES: Cc1cc(NC(=O)Nc2cc([C@@H](C)CC(=O)O)ccc2N(CC(C)C)CC(C)C)no1]

Example 44 was prepared following the procedure for Example 35 using the 35C enantiomer 2 and 5-methylisox-azol-3-amine Anal. Calc'd for $C_{23}H_{34}N_4O_4$ 430.26, found [M+H] 431.4, $T_r$=1.02 min (Method B). $^1H$ NMR (500 MHz, METHANOL-$d_4$) δ 7.88 (d, J=2.0 Hz, 1H), 7.09 (d, J=8.4 Hz, 1H), 6.89 (dd, J=7.9, 2.0 Hz, 1H), 6.30 (s, 1H), 3.25-3.13 (m, 1H), 2.65 (d, J=6.9 Hz, 4H), 2.60 (dd, J=15.1, 6.2 Hz, 1H), 2.47 (dd, J=15.1, 8.7 Hz, 1H), 2.37 (s, 3H), 1.68 (dt, J=13.4, 6.7 Hz, 2H), 1.29 (d, J=6.9 Hz, 3H), 0.85 (d, J=6.4 Hz, 12H)

Example 45

(R)-3-(3-(2-(4-cyanophenyl)acetamido)-4-(diisobutylamino)phenyl)butanoic acid

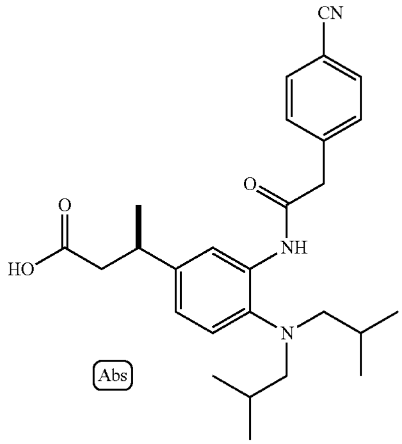 [SMILES: CC(C)CN(CC(C)C)c1ccc([C@H](C)CC(=O)O)cc1NC(=O)Cc1ccc(C#N)cc1]

To a solution of 35C enantiomer 1 (0.030 g, 0.094 mmol) in DMF (0.936 ml) was added 2-(4-cyanophenyl)acetic acid (0.030 g, 0.187 mmol), 1H-benzo[d][1,2,3]triazol-1-ol (0.025 g, 0.187 mmol), HOBT (0.029 g, 0.187 mmol) and EDC (0.036 g, 0.187 mmol). This mixture was stirred at RT for 10 minutes and then DIEA (0.049 ml, 0.281 mmol) was added. The reaction was stirred at RT for 3 h and then diluted with EtOAc. This was then washed once with 1 N HCl, twice with water and once with brine. The organics were dried over $MgSO_4$, filtered and concentrated to give the crude product as a yellow solid. To this material was added 2.0 mL THF, 0.4 mL MeOH and 0.4 mL 1 N NaOH. This mixture was heated at 55° C. for 72 hours and then cooled to RT and 0.5 mL of 1N HCl was added to neutralize the solution and this was extracted thrice with EtOAc. The organics were dried over $MgSO_4$, filtered and concentrated to give the crude acid. The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to yield Example 45 (21.9 mg, 0.048 mmol, 51%). LC-MS Anal. Calc'd for $C_{27}H_{35}N_3O_3$ 449.6, found [M+H] 450.3, $T_r$=1.957 min (Method E).

Example 46

3-(4-(diisobutylamino)-3-(3-(3-(trifluoromethyl)isoxazol-5-yl)ureido)phenyl)butanoic acid Racemic

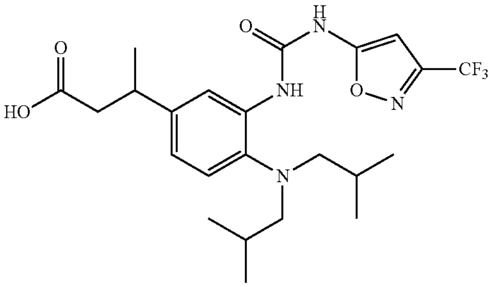 [SMILES: CC(C)CN(CC(C)C)c1ccc(C(C)CC(=O)O)cc1NC(=O)Nc1cc(C(F)(F)F)no1]

Example 46 was prepared following the procedure for Example 3. Anal. Calc'd for $C_{23}H_{31}F_3N_4O_4$ 484.23, found [M+H] 485.5, $T_r$=1.02 min (Method B) $^1$H NMR (500 MHz, DMSO-$d_6$) δ 8.34-8.23 (m, 1H), 7.94-7.84 (m, 1H), 7.25-7.15 (m, 1H), 6.99-6.87 (m, 1H), 3.16-3.02 (m, 1H), 2.64 (d, J=6.9 Hz, 4H), 2.48-2.39 (m, 2H), 1.70-1.52 (m, 2H), 1.28-1.11 (m, 3H), 0.86 (d, J=6.4 Hz, 12H).

Example 47

3-(3-(3-(3-cyclopropylisoxazol-5-yl)ureido)-4-(diisobutylamino)phenyl)butanoic acid Racemic

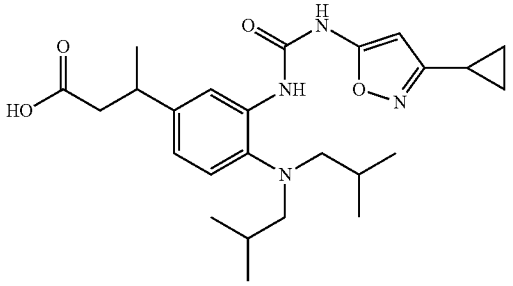 [SMILES: CC(C)CN(CC(C)C)c1ccc(C(C)CC(=O)O)cc1NC(=O)Nc1cc(C2CC2)no1]

Example 47 was prepared following the procedure for Example 3. LC-MS Anal. Calc'd for $C_{25}H_{36}N_4O_4$ 456.27, found [M+H] 457.20, $T_r$=3.61 min (Method A) $^1$H NMR (500 MHz, DMSO-$d_6$) δ 8.16 (s, 1H), 7.86 (d, J=2.0 Hz, 1H), 7.15 (d, J=7.9 Hz, 1H), 6.89 (dd, J=8.2, 1.7 Hz, 1H), 5.81 (s, 1H), 3.12-3.01 (m, 1H), 2.61 (d, J=6.9 Hz, 4H), 2.47-2.28 (m, 2H), 1.95-1.85 (m, 1H), 1.60 (tq, J=13.2, 6.6 Hz, 2H), 1.17 (d, J=6.9 Hz, 3H), 1.02-0.91 (m, 2H), 0.87-0.80 (m, 12H), 0.77-0.71 (m, 2H).

Example 48

3-(4-(diisobutylamino)-3-(3-(5-methylisoxazol-3-yl)ureido)phenyl)butanoic acid

Racemic

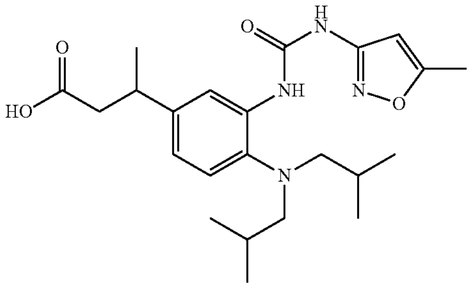 [SMILES: Cc1cc(NC(=O)Nc2cc(C(C)CC(=O)O)ccc2N(CC(C)C)CC(C)C)no1]

Example 48 was prepared following the procedure for Example 3. LC-MS Anal. Calc'd for $C_{23}H_{34}N_4O_4$ 430.26, found [M+H] 431.20, $T_r$=3.53 min (Method A) $^1$H NMR (500 MHz, METHANOL-$d_4$) δ 7.89 (d, J=2.0 Hz, 1H), 7.09 (d, J=8.4 Hz, 1H), 6.89 (dd, J=7.9, 2.0 Hz, 1H), 6.29 (s, 1H), 3.25-3.15 (m, 1H), 2.65 (d, J=6.9 Hz, 4H), 2.60 (dd, J=14.9, 6.4 Hz, 1H), 2.51-2.43 (m, 1H), 2.37 (s, 3H), 1.75-1.64 (m, 2H), 1.29 (d, J=6.9 Hz, 3H), 0.85 (d, J=6.9 Hz, 12H).

Example 49

Racemic 3-(4-(cyclohexyl(isobutyl)amino)-3-(3-(p-tolyl)ureido)phenyl)butanoic acid

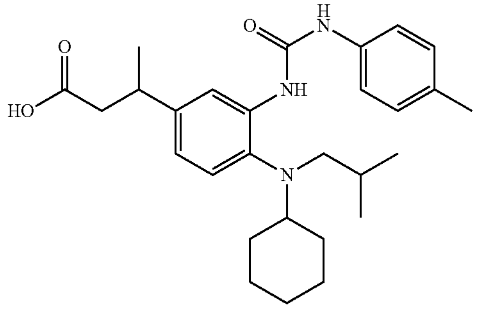 [SMILES: Cc1ccc(NC(=O)Nc2cc(C(C)CC(=O)O)ccc2N(CC(C)C)C2CCCCC2)cc1]

49A: 1-(5-bromo-2-(cyclohexyl(isobutyl)amino)phenyl)-3-(p-tolyl)urea

To a solution of cyclohexanamine (2.309 mL, 20.17 mmol) in DCM (100 mL) cooled to 0° C. was added TEA (4.22 mL, 30.2 mmol). The mixture was stirred at 0° C. for 5 min before isobutyryl chloride (2.54 mL, 24.20 mmol) was added dropwise. The mixture was stirred and allowed to warm to room temperature slowly. After 2 h, LC/MS indicated completion. The reaction mixture was quenched with saturated aqueous sodium bicarbonate then extracted with dichloromethane. The combined organic extracts were washed with 1N aqueous HCl, brine then dried over $Na_2SO_4$, filtered and concentrated in vacuo to afford 3.5 g of N-cyclohexylisobutyramide as a white solid. This was used without purification. To a solution of above obtained N-cyclohexylisobutyramide (2.3 g, 13.59 mmol) in THF (50 mL) was slowly added LAH (27.2 mL, 27.2 mmol). The resulting solution was refluxed at 70° C. for 16 h. LC/MS indicated depletion of SM. After Fieser quench, the solid was filtered out. After separating two layers, the aqueous layer was further extracted with EtOAc and the combined organic layer was washed with water, brine, dried over $MgSO_4$, filtered and concentrated to give 2 g of N-isobutylcyclohexanamine. This was used without purification. To a solution of above obtained N-isobutylcyclohexanamine (1.412 g, 9.09 mmol) in NMP (2 mL) was added 4-bromo-1-fluoro-2-nitrobenzene (1 g, 4.55 mmol) and Hunig's base (2.382 mL, 13.64 mmol). The resulting solution was heated at 120° C. for 6 h. LC/MS indicated desired product. After cooling to room temperature, it was filtered through a pad of Celite, rinsed with EtOAc. After concentration, purification via silica gel chromatography gave 4-bromo-N-cyclohexyl-N-isobutyl-2-nitroaniline (orange solid, 0.85 g, 2.60 mmol, 42.8% yield). To a stirred solution of above obtained 4-bromo-N-cyclohexyl-N-isobutyl-2-nitroaniline (570 mg, 1.444 mmol) in MeOH (10.00 mL) cooled in an ice-water bath was added ammonium chloride (1545 mg, 28.9 mmol) and zinc (944 mg, 14.44 mmol). After stirring for 5 min, water (1.0 mL) was added and the reaction mixture was stirred for 2 h. LC/MS indicated desired product. Saturated aqueous sodium bicarbonate was added and the suspension was then filtered through a pad of celite. The filter cake was rinsed with EtOAc. The aqueous layer was further extracted with EtOAc and the combined organic layer was washed with water, brine, dried over $MgSO_4$, filtered and concentrated. Purification via silica gel chromatography gave 4-bromo-N1-cyclohexyl-N1-isobutylbenzene-1,2-diamine (yellow oil, 400 mg, 1.230 mmol, 85% yield). To a solution of above obtained 4-bromo-N1-cyclohexyl-N1-isobutylbenzene-1,2-diamine (200 mg, 0.615 mmol) in THF (16 mL) was added 1-isocyanato-4-methylbenzene (123 mg, 0.922 mmol). The resulting solution was stirred at room temperature for 16 h. LC/MS indicated desired peak and completion. The reaction mixture was concentrated and purification via silica gel chromatography gave 49A (white solid, 130 mg, 0.284 mmol, 46.1% yield). LC-MS Anal. Calc'd for $C_{24}H_{32}BrN_3O$ 457.17. found [M+3H] 459.91. $T_r$=4.32 min (Method A). $^1$H NMR (400 MHz, CHLOROFORM-d) δ 8.52 (d, J=2.2 Hz, 1H), 7.25-7.15 (m, 4H), 7.06 (dd, J=8.5, 2.3 Hz, 1H), 6.93 (d, J=8.6 Hz, 1H), 2.61 (br. s., 2H), 2.37 (s, 3H), 2.33-2.23 (m, 1H), 1.63 (br. s., 2H), 1.59-1.51 (m, 1H), 1.38-1.22 (m, 3H), 1.12-0.93 (m, 5H), 0.71 (d, J=6.6 Hz, 6H)

49B: 3-(4-(cyclohexyl(isobutyl)amino)-3-(3-(p-tolyl)ureido)phenyl)butanoic acid

To a solution of 49A (70 mg, 0.153 mmol) in DMF (1.5 mL) at room temperature was added (E)-methyl but-2-enoate (0.049 mL, 0.458 mmol), Tetrabutylammonium bromide (9.84 mg, 0.031 mmol), triethylamine (0.043 mL, 0.305 mmol) and dichlorobis(tri-o-tolylphosphine)-palladium(II) (6.00 mg, 7.63 μmol). The mixture was purged with nitrogen for 5 min. Then it was sealed and stirred at 110° C. for 6 h. LC/MS indicated desired product. It was then cooled to room temperature, purification of the crude material via silica gel chromatography gave 50 mg unsaturated ester. This was dissolved in MeOH (5 mL), then Pd on carbon (32.5 mg, 0.031 mmol) was added. The suspension was hydrogenated (1 atm, balloon) for 1 h. LC/MS indicated product. The suspension was filtered through a pad of celite and the filter cake was rinsed with EtOAc (2×20 mL). Combined filtrate and rinses were concentrated in vacuo. This was then dissolved in THF (1.5 mL), then NaOH (0.458 mL, 0.458 mmol) was added. MeOH was added and it turned into a clear yellow/orange solution. The reaction was monitored by LC/MS. After 16 h, reaction was complete by LC/MS. Then most MeOH and THF was removed in vacuo and the crude was diluted with 5 mL of water. The pH of the aqueous layer was adjusted to 4 using 1N aqueous HCl. The aqueous phase was then extracted with EtOAc (2×10 mL) and the combined organic phase was washed with brine, dried over $Na_2SO_4$, filtered and concentrated. Preparative HPLC purification gave 49B (yellow oil, 18.8 mg, 0.038 mmol, 25% yield). LC-MS Anal. Calc'd for $C_{28}H_{39}N_3O_3$ 465.30, found [M+H] 466.22, $T_r$=3.41 min (Method A) $^1$H NMR (500 MHz, DMSO-$d_6$) δ 9.40 (s, 1H), 8.01-7.93 (m, 2H), 7.36 (d, J=8.4 Hz, 2H), 7.12-7.05 (m, 3H), 6.81 (dd, J=8.2, 1.7 Hz, 1H), 3.12-3.01 (m, 1H), 2.85-2.66 (m, 2H), 2.47-2.36 (m, 1H), 2.24 (s, 3H), 1.87 (d, J=10.9 Hz, 2H), 1.68 (d, J=11.9 Hz, 2H), 1.51 (d, J=12.4 Hz, 1H), 1.29 (dt, J=13.0, 6.6 Hz, 1H), 1.20 (d, J=6.9 Hz, 4H), 1.14-0.94 (m, 3H), 0.81 (d, J=6.4 Hz, 6H) (one proton buried under DMSO solvent peak).

Evaluation of Biological Activity

Exemplary compounds were tested for inhibition of IDO activity. Experimental procedures and results are provided below.

IDO Kynurenine Assay with Human IDO1/HEK293 Cells

Human IDO1/HEK293 cells were seeded at 10,000 cells per 50 uL per well with RPMI/phenol red free media contains 10% FBS in a 384-well black wall clear bottom tissue culture plate (Matrix Technologies LLC) 125 nL of certain concentration of compound was then added to each well using ECHO liquid handling systems. The cells were incubated for 20 hours in 37° C. incubator with 5% $CO_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Results of the IDO assays are shown in the table below.

TABLE 1

HEK Human IDO-1

| Example # | HEK Human IDO-1 $IC_{50}$ (nM) |
|---|---|
| 2 | 205 |
| 13 | 3 |
| 30 | 0.7 |
| 37 | 11 |
| 38 | 29 |
| 39 | 169 |
| 40 | 22 |
| 43 | 17 |
| 44 | 87 |
| 45 | 5 |
| 46 | 7 |
| 49 | 1 |

What is claimed is:

1. A compound of formula I (I)

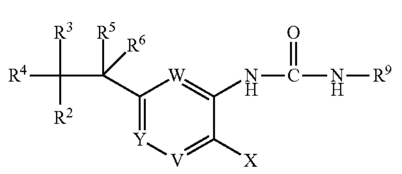

wherein

X is

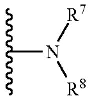

or

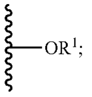

W is N or $CR^{10}$;

Y is N or $CR^{11}$;

V is N or $CR^{12}$;

$R^1$ is optionally substituted aryl-$C_1$-$C_{10}$-alkyl, or optionally substituted aryl;

$R^2$ is —$CO_2H$, optionally substituted heterocyclyl, optionally substituted —$CONHSO_2R^{14}$, optionally substituted —$CONHCOR^{13}$, optionally substituted —$SO_2NHCOR^{13}$ or optionally substituted —$NHSO_2R^{14}$;

$R^{13}$ is optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^{14}$ is $CF_3$ or optionally substituted $C_1$-$C_{10}$ alkyl;

$R^3$ is H, halo, CN, optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^4$ is H or optionally substituted $C_1$-$C_{10}$ alkyl;

$R^5$ and $R^6$ are independently H, optionally substituted $C_1$-$C_{10}$ alkyl or OH, or $R^5$ and $R^6$ are taken together with the carbon to which they are attached to form

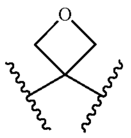

;

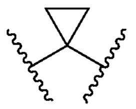

$R^7$ and $R^8$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, or optionally substituted $C_3$-$C_8$ cycloalkyl;

$R^9$ is optionally substituted aryl, optionally substituted $C_1$-$C_{10}$ alkylaryl, optionally substituted $C_1$-$C_{10}$ alkoxyaryl, optionally substituted heteroaryl, optionally substituted $C_1$-$C_{10}$-alkyl heteroaryl, optionally substituted aryl-$C_1$-$C_{10}$-alkylaryl, optionally substituted aryloxyaryl, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, or optionally substituted $C_4$-$C_8$ cycloalkenyl;

$R^{10}$, $R^{11}$ and $R^{12}$ are H;

and/or a stereoisomer, a tautomer or a pharmaceutically acceptable salt thereof.

2. The compound according to claim 1 of formula II

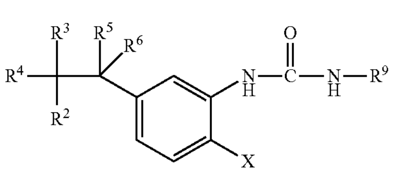

(II)

wherein

X is

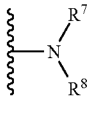

or

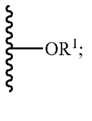

$R^1$ is optionally substituted aryl-$C_1$-$C_{10}$-alkyl, or optionally substituted aryl;

$R^2$ is —$CO_2H$, optionally substituted heterocyclyl, optionally substituted —$CONHSO_2R^{14}$, optionally substituted —$CONHCOR^{13}$, optionally substituted —$SO_2NHCOR^{13}$ or optionally substituted —$NHSO_2R^{14}$;

$R^{13}$ is optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^{14}$ is $CF_3$ or optionally substituted $C_1$-$C_{10}$ alkyl;

$R^3$ is H, halo, CN, optionally substituted $C_1$-$C_{10}$ alkyl, optionally substituted $C_3$-$C_8$ cycloalkyl, optionally substituted $C_2$-$C_{10}$ alkenyl or optionally substituted $C_2$-$C_{10}$ alkynyl;

$R^4$ is H or optionally substituted $C_1$-$C_{10}$ alkyl;

$R^5$ and $R^6$ are independently H, optionally substituted $C_1$-$C_{10}$ alkyl or OH, or $R^5$ and $R^6$ are taken together with the carbon to which they are attached to form

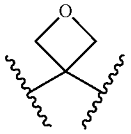

;

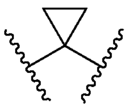

$R^7$ and $R^8$ are independently H, optionally substituted $C_1$-$C_{10}$ alkyl, optionally substituted $C_1$-$C_{10}$-alkoxy-$C_1$-$C_{10}$-alkyl, optionally substituted $C_1$-$C_{10}$ alkoxy, optionally substituted aryl, optionally substituted aryl-$C_1$-$C_{10}$-alkyl, optionally substituted 5- to 8-membered heteroaryl, or optionally substituted $C_3$-$C_8$ cycloalkyl;

$R^9$ is optionally substituted aryl, optionally substituted $C_1$-$C_{10}$ alkylaryl, optionally substituted $C_1$-$C_{10}$ alkoxyaryl, optionally substituted heteroaryl, optionally substituted $C_1$-$C_{10}$-alkyl heteroaryl, optionally substituted aryl-$C_1$-$C_{10}$-alkylaryl, optionally substituted aryloxyaryl, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_8$ cycloalkyl, or optionally substituted $C_4$-$C_8$ cycloalkenyl;

$R^{10}$, $R^{11}$ and $R^{12}$ are H;

and/or a stereoisomer, a tautomer or a pharmaceutically acceptable salt thereof.

3. The compound according to claim 2 wherein X is $NR^7R^8$ and/or a stereoisomer, a tautomer or a pharmaceutically acceptable salt thereof.

4. The compound according to claim 2 wherein X is $OR^1$ and/or a stereoisomer, a tautomer or a pharmaceutically acceptable salt thereof.

5. The compound according to claim 3 wherein

X is $NR^7R^8$;

$R^2$ is $CO_2H$ or

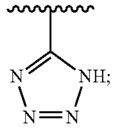

$R^3$ is H or $C_1$-$C_6$ alkyl;

$R^4$ is H or $C_1$-$C_6$ alkyl;

$R^5$ and $R^6$ are independently H, $C_1$-$C_6$ alkyl, $CF_3$ or OH, or $R^5$ and $R^6$ are taken together with the carbon to which they are attached to form

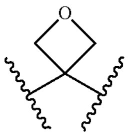

;

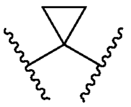

$R^7$ and $R^8$ are independently selected from $C_1$-$C_6$ alkyl, $C_1$-$C_6$-alkoxy-$C_1$-$C_{10}$ alkyl, $C_1$-$C_6$ alkoxy, or optionally substituted aryl-$C_1$-$C_6$-alkyl;

$R^9$ is aryl, $C_1$-$C_6$ alkylaryl, $C_1$-$C_6$ alkoxyaryl, or optionally substituted heteroaryl;

and/or a stereoisomer, a tautomer or a pharmaceutically acceptable salt thereof.

6. The compound according to claim 4 wherein

X is $OR^1$;

$R^1$ is aryl-$C_1$-$C_6$-alkyl or aryl($C_3$-$C_8$ cycloalkyl)$C_1$-$C_6$ alkyl;

$R^2$ is $CO_2H$;

$R^3$ is H;

$R^4$ is H;

$R^5$ and $R^6$ are independently selected from H or $C_1$-$C_6$ alkyl;

$R^9$ is $C_1$-$C_6$ alkylaryl or haloaryl;

and/or a stereoisomer, a tautomer or a pharmaceutically acceptable salt thereof.

7. The compound according to claim 1 which is 3-(4-(diisobutylamino)-3-(3-(3-methylisoxazol-5-yl)ureido)phenyl)butanoic acid, and/or a stereoisomer, a tautomer or a pharmaceutically acceptable salt thereof.

8. A pharmaceutical composition comprising one or more compounds according to claim 1 and a pharmaceutically acceptable carrier or diluent.

9. A method of inhibiting the activity of indoleamine 2,3-dioxygenase comprising contacting said indoleamine 2,3-dioxygenase with a compound according to claim 1, or a pharmaceutically acceptable salt thereof.

10. The compound of claim 1 that is
3-(4-(diisobutylamino)-3-(3-(p-toly)ureido)phenyl)-2-methylpropanoic acid;
2-(3-(4-(diisobutylamino)-3-(3-(p-tolyl)ureido)phenyl) oxetan-3-yl)acetic acid;
3-(4-(diisobutylamino)-3-(3-(p-tolyl)ureido)phenyl)butanoic acid;
3-(4-(diisobutylamino)-3-(3-(2-fluorophenyl)ureido)phenyl)butanoic acid;
3-(3-(3-(4-chloro-2-fluorophenyl)ureido)-4-(diisobutylamino)phenyl)butanoic acid;
3-(4-(diisobutylamino)-3-(3-(4-ethoxyphenyl)ureido) phenyl)butanoic acid;
3-(4-(diisobutylamino)-3-(3-(6-methylpyridin-3-yl) ureido)phenyl)butanoic acid;
3-(4-((4-chlorobenzyl)(2-methoxyethyl)amino)-3-(3-(p-toly)ureido)phenyl)butanoic acid;
3-(3-(3-(2-fluorophenyl)ureido)-4-(1-phenylpropoxy) phenyl)butanoic acid;
3-(4-(1-phenylpropoxy)-3-(3-(p-toly)ureido)phenyl)butanoic acid;
3-(4-(cyclopropyl(phenyl)methoxy)-3-(3-(p-toly)ureido) phenyl)butanoic acid;
3-(4-(3-5 phenylpropoxy)-3-(3-(p-tolyl)ureido)phenyl) butanoic acid; 3-(4-(diisobutylamino)-3-(3-(3-methylisoxazol-5-yl)ureido)phenyl)butanoic acid;
3-(4-(diisobutylamino)-3-(3-(p-toly)ureido)phenyl)-4,4,4-trifluorobutanoic acid;
3-(4-(diisobutylamino)-3-(3-(2-fluorophenyl)ureido)phenyl)-4,4,4-trifluorobutanoic acid;
3-(4-(diisobutylamino)-3-(3-(4-phenoxyphenyl)ureido) phenyl)-4,4,4-trifluorobutanoic acid;
3-(3-(3-(4-chlorophenyl)ureido)-4-(diisobutylamino)phenyl)-4,4,4-trifluorobutanoic acid;
3-(4-(diisobutylamino)-3-(3-(4-fluorophenyl)ureido)phenyl)-4,4,4-trifluorobutanoic acid;
3-(3-(3-(2,4-dichlorophenyl)ureido)-4-(diisobutylamino) phenyl)-4,4,4-trifluorobutanoic acid;
3-(4-(diisobutylamino)-3-(3-phenylureido)phenyl)-4,4,4-trifluorobutanoic acid;
3-(4-(diisobutylamino)-3-(3-(4-isopropylphenyl)ureido) phenyl)-4,4,4-trifluorobutanoic acid;
3-(4-(diisobutylamino)-3-(3-(4-ethylphenyl)ureido)phenyl)-4,4,4-trifluorobutanoic acid;
3-(4-(diisobutylamino)-3-(3-(4-(trifluoromethyl)phenyl) ureido)phenyl)-4,4,4-trifluorobutanoic acid;
3-(4-(diisobutylamino)-3-(3-(4-methoxyphenyl)ureido) phenyl)-4,4,4-trifluorobutanoic acid;
3-(4-(diisobutylamino)-3-(3-(o-toly)ureido)phenyl)-4,4,4-trifluorobutanoic acid;
3-(3-(3-(2-chloro-4-methylphenyl)ureido)-4-(diisobutylamino)phenyl)-4,4,4-trifluorobutanoic acid;
3-(3-(3-(4-benzylphenyl)ureido)-4-(diisobutylamino) phenyl)-4,4,4-trifluorobutanoic acid;
3-(3-(3-(4-(difluoromethoxy)phenyl)ureido)-4-(diisobutylamino)phenyl)-4,4,4-trifluorobutanoic acid;
3-(4-(diisobutylamino)-3-(3-(4-ethoxyphenyl)ureido) phenyl)-4,4,4-trifluorobutanoic acid;
3-(3-(3-(2,4-difluorophenyl)ureido)-4-(diisobutylamino) phenyl)-4,4,4-trifluorobutanoic acid;
3-(4-(diisobutylamino)-3-(3-(m-toly)ureido)phenyl)-4,4,4-trifluorobutanoic acid;
1-(5-(2-(1H-tetrazol-5-yl)ethyl)-2-(diisobutylamino)phenyl)-3-(p-tolyl)urea;
1-(5-(2-(1H-tetrazol-5-yl)ethyl)-2-(diisobutylamino)phenyl)-3-(4-fluorophenyl)urea;
2-(1-(4-(diisobutylamino)-3-(3-(p-tolyl)ureido)phenyl) cyclopropyl)acetic acid;
(R)-3-(4-(diisobutylamino)-3-(3-(quinoxalin-6-yl)ureido) phenyl)butanoic acid;
(S)-3-(4-(diisobutylamino)-3-(3-(quinoxalin-6-yl)ureido) phenyl)butanoic acid;
(R)-3-(4-(diisobutylamino)-3-(3-(pyrimidin-5-yl)ureido) phenyl)butanoic acid;
(S)-3-(4-(diisobutylamino)-3-(3-(pyrimidin-5-yl)ureido) phenyl)butanoic acid;
(S)-3-(4-(diisobutylamino)-3-(3-(2-5 methylpyrimidin-5-yl)ureido)phenyl)butanoic acid;
(R)-3-(4-(diisobutylamino)-3-(3-(2-methylpyrimidin-5-yl)ureido)phenyl)butanoic acid;
(R)-3-(4-(diisobutylamino)-3-(3-(p-toly)ureido)phenyl) butanoic acid;
(R)-3-(4-(diisobutylamino)-3-(3-(5-methylisoxazol-3-yl) ureido)phenyl)butanoic acid; (S)-3-(4-(diisobutylamino)-3-(3-(p-toly)ureido)phenyl)butanoic acid;
(S)-3-(4-(diisobutylamino)-3-(3-(5-methylisoxazol-3-yl) ureido)phenyl)butanoic acid;
(R)-3-(3-(2-(4-cyanophenyl)acetamido)-4-(diisobutylamino)phenyl)butanoic acid;
3-(4-(diisobutylamino)-3-(3-(3-(trifluoromethyl)isoxazol-5-yl)ureido)phenyl)butanoic acid;
3-(3-(3-(3-cyclopropylisoxazol-5-yl)ureido)-4-(diisobutylamino)phenyl)butanoic acid;
3-(4-(diisobutylamino)-3-(3-(5-methylisoxazol-3-yl) ureido)phenyl)butanoic acid;
or 3-(4-(cyclohexyl(isobutyl)amino)-3-(3-(p-tolyl) ureido)phenyl)butanoic acid; and/or a stereoisomer, a tautomer or a pharmaceutically acceptable salt thereof.

11. The method of claim 9 comprising contacting said indoleamine 2,3-dioxygenase with a compound according to claim 1 that is
3-(4-(diisobutylamino)-3-(3-(p-toly)ureido)phenyl)-2-methylpropanoic acid;
2-(3-(4-(diisobutylamino)-3-(3-(p-tolyl)ureido)phenyl) oxetan-3-yl)acetic acid;
3-(4-(diisobutylamino)-3-(3-(p-tolyl)ureido)phenyl)butanoic acid;
3-(4-(diisobutylamino)-3-(3-(2-fluorophenyl)ureido)phenyl)butanoic acid;
3-(3-(3-(4-chloro-2-fluorophenyl)ureido)-4-(diisobutylamino)phenyl)butanoic acid;
3-(4-(diisobutylamino)-3-(3-(4-ethoxyphenyl)ureido) phenyl)butanoic acid;
3-(4-(diisobutylamino)-3-(3-(6-methylpyridin-3-yl) ureido)phenyl)butanoic acid;
3-(4-((4-chlorobenzyl)(2-methoxyethyl)amino)-3-(3-(p-toly)ureido)phenyl)butanoic acid;
3-(3-(3-(2-fluorophenyl)ureido)-4-(1-phenylpropoxy) phenyl)butanoic acid;
3-(4-(1-phenylpropoxy)-3-(3-(p-toly)ureido)phenyl)butanoic acid;
3-(4-(cyclopropyl(phenyl)methoxy)-3-(3-(p-toly)ureido) phenyl)butanoic acid;
3-(4-(3-5 phenylpropoxy)-3-(3-(p-tolyl)ureido)phenyl) butanoic acid; 3-(4-(diisobutylamino)-3-(3-(3-methylisoxazol-5-yl)ureido)phenyl)butanoic acid;
3-(4-(diisobutylamino)-3-(3-(p-toly)ureido)phenyl)-4,4,4-trifluorobutanoic acid;
3-(4-(diisobutylamino)-3-(3-(2-fluorophenyl)ureido)phenyl)-4,4,4-trifluorobutanoic acid;
3-(4-(diisobutylamino)-3-(3-(4-phenoxyphenyl)ureido) phenyl)-4,4,4-trifluorobutanoic acid;

3-(3-(3-(4-chlorophenyl)ureido)-4-(diisobutylamino)phenyl)-4,4,4-trifluorobutanoic acid;

3-(4-(diisobutylamino)-3-(3-(4-fluorophenyl)ureido)phenyl)-4,4,4-trifluorobutanoic acid;

3-(3-(3-(2,4-dichlorophenyl)ureido)-4-(diisobutylamino)phenyl)-4,4,4-trifluorobutanoic acid;

3-(4-(diisobutylamino)-3-(3-phenylureido)phenyl)-4,4,4-trifluorobutanoic acid;

3-(4-(diisobutylamino)-3-(3-(4-isopropylphenyl)ureido)phenyl)-4,4,4-trifluorobutanoic acid;

3-(4-(diisobutylamino)-3-(3-(4-ethylphenyl)ureido)phenyl)-4,4,4-trifluorobutanoic acid;

3-(4-(diisobutylamino)-3-(3-(4-(trifluoromethyl)phenyl)ureido)phenyl)-4,4,4-trifluorobutanoic acid;

3-(4-(diisobutylamino)-3-(3-(4-methoxyphenyl)ureido)phenyl)-4,4,4-trifluorobutanoic acid;

3-(4-(diisobutylamino)-3-(3-(o-toly)ureido)phenyl)-4,4,4-trifluorobutanoic acid;

3-(3-(3-(2-chloro-4-methylphenyl)ureido)-4-(diisobutylamino)phenyl)-4,4,4-trifluorobutanoic acid;

3-(3-(3-(4-benzylphenyl)ureido)-4-(diisobutylamino)phenyl)-4,4,4-trifluorobutanoic acid;

3-(3-(3-(4-(difluoromethoxy)phenyl)ureido)-4-(diisobutylamino)phenyl)-4,4,4-trifluorobutanoic acid;

3-(4-(diisobutylamino)-3-(3-(4-ethoxyphenyl)ureido)phenyl)-4,4,4-trifluorobutanoic acid;

3-(3-(3-(2,4-difluorophenyl)ureido)-4-(diisobutylamino)phenyl)-4,4,4-trifluorobutanoic acid;

3-(4-(diisobutylamino)-3-(3-(m-toly)ureido)phenyl)-4,4,4-trifluorobutanoic acid;

1-(5-(2-(1H-tetrazol-5-yl)ethyl)-2-(diisobutylamino)phenyl)-3-(p-tolyl)urea;

1-(5-(2-(1H-tetrazol-5-yl)ethyl)-2-(diisobutylamino)phenyl)-3-(4-fluorophenyl)urea;

2-(1-(4-(diisobutylamino)-3-(3-(p-tolyl)ureido)phenyl)cyclopropyl)acetic acid;

(R)-3-(4-(diisobutylamino)-3-(3-(quinoxalin-6-yl)ureido)phenyl)butanoic acid;

(S)-3-(4-(diisobutylamino)-3-(3-(quinoxalin-6-yl)ureido)phenyl)butanoic acid;

(R)-3-(4-(diisobutylamino)-3-(3-(pyrimidin-5-yl)ureido)phenyl)butanoic acid;

(S)-3-(4-(diisobutylamino)-3-(3-(pyrimidin-5-yl)ureido)phenyl)butanoic acid;

(S)-3-(4-(diisobutylamino)-3-(3-(2-5 methylpyrimidin-5-yl)ureido)phenyl)butanoic acid;

(R)-3-(4-(diisobutylamino)-3-(3-(2-methylpyrimidin-5-yl)ureido)phenyl)butanoic acid;

(R)-3-(4-(diisobutylamino)-3-(3-(p-toly)ureido)phenyl)butanoic acid;

(R)-3-(4-(diisobutylamino)-3-(3-(5-methylisoxazol-3-yl)ureido)phenyl)butanoic acid; (S)-3-(4-(diisobutylamino)-3-(3-(p-toly)ureido)phenyl)butanoic acid;

(S)-3-(4-(diisobutylamino)-3-(3-(5-methylisoxazol-3-yl)ureido)phenyl)butanoic acid;

(R)-3-(3-(2-(4-cyanophenyl)acetamido)-4-(diisobutylamino)phenyl)butanoic acid;

3-(4-(diisobutylamino)-3-(3-(3-(trifluoromethyl)isoxazol-5-yl)ureido)phenyl)butanoic acid;

3-(3-(3-(3-cyclopropylisoxazol-5-yl)ureido)-4-(diisobutylamino)phenyl)butanoic acid;

3-(4-(diisobutylamino)-3-(3-(5-methylisoxazol-3-yl)ureido)phenyl)butanoic acid;

or 3-(4-(cyclohexyl(isobutyl)amino)-3-(3-(p-tolyl)ureido)phenyl)butanoic acid, or a pharmaceutically acceptable salt thereof.

* * * * *

UNITED STATES PATENT AND TRADEMARK OFFICE

CERTIFICATE OF CORRECTION

PATENT NO. : 9,624,188 B2
APPLICATION NO. : 14/775976
DATED : April 18, 2017
INVENTOR(S) : James Aaron Balog et al.

It is certified that error appears in the above-identified patent and that said Letters Patent is hereby corrected as shown below:

In the Claims

Claim 10, Column 75, Line 2, delete "(p-toly)" and insert -- (p-tolyl) --, therefor.

Claim 10, Column 75, Lines 17-18, delete "(p-toly)" and insert -- (p-tolyl) --, therefor.

Claim 10, Column 75, Line 21, delete "(p-toly)" and insert -- (p-tolyl) --, therefor.

Claim 10, Column 75, Line 23, delete "(p-toly)" and insert -- (p-tolyl) --, therefor.

Claim 10, Column 75, Line 25, delete "(3-5 phenylpropoxy)" and insert -- (3-phenylpropoxy) --, therefor.

Claim 10, Column 75, Line 28, delete "(p-toly)" and insert -- (p-tolyl) --, therefor.

Claim 10, Column 75, Line 50, delete "(o-toly)" and insert -- (o-tolyl) --, therefor.

Claim 10, Column 75, Line 62, delete "(m-toly)" and insert -- (m-tolyl) --, therefor.

Claim 10, Column 76, Line 11, delete "(2-5 methylpyrimidin-5-)" and insert -- (2-methylpyrimidin-5-) --, therefor.

Claim 10, Column 76, Line 16, delete "(p-toly)" and insert -- (p-tolyl) --, therefor.

Claim 10, Column 76, Line 20, delete "(p-toly)" and insert -- (p-tolyl) --, therefor.

Claim 11, Column 76, Line 37, delete "(p-toly)" and insert -- (p-tolyl) --, therefor.

Claim 11, Column 76, Lines 51-52, delete "(p-toly)" and insert -- (p-tolyl) --, therefor.

Signed and Sealed this
Thirtieth Day of January, 2018

Joseph Matal

Joseph Matal
*Performing the Functions and Duties of the*
*Under Secretary of Commerce for Intellectual Property and*
*Director of the United States Patent and Trademark Office*

Claim 11, Column 76, Line 55, delete "(p-toly)" and insert -- (p-tolyl) --, therefor.

Claim 11, Column 76, Line 57, delete "(p-toly)" and insert -- (p-tolyl) --, therefor.

Claim 11, Column 76, Line 59, delete "(3-5 phenylpropoxy)" and insert -- (3-phenylpropoxy) --, therefor.

Claim 11, Column 76, Line 62, delete "(p-toly)" and insert -- (p-tolyl) --, therefor.

Claim 11, Column 77, Line 17, delete "(o-toly)" and insert -- (o-tolyl) --, therefor.

Claim 11, Column 77, Line 29, delete "(m-toly)" and insert -- (m-tolyl) --, therefor.

Claim 11, Column 78, Line 11, delete "(2-5 methylpyrimidin-5-)" and insert -- (2-methylpyrimidin-5-) --, therefor.

Claim 11, Column 78, Line 15, delete "(p-toly)" and insert -- (p-tolyl) --, therefor.

Claim 11, Column 78, Line 19, delete "(p-toly)" and insert -- (p-tolyl) --, therefor.